United States Patent
Goodman et al.

(10) Patent No.: US 12,161,701 B2
(45) Date of Patent: Dec. 10, 2024

(54) COMPOSITIONS AND METHODS FOR ENZYMATIC DISRUPTION OF BACTERIAL BIOFILMS

(71) Applicant: RESEARCH INSTITUTE AT NATIONWIDE CHILDREN'S HOSPITAL, Columbus, OH (US)

(72) Inventors: Steven David Goodman, Columbus, OH (US); Lauren Opremcak Bakaletz, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 548 days.

(21) Appl. No.: 17/282,341

(22) PCT Filed: Oct. 4, 2019

(86) PCT No.: PCT/US2019/054868
§ 371 (c)(1),
(2) Date: Apr. 1, 2021

(87) PCT Pub. No.: WO2020/073004
PCT Pub. Date: Apr. 9, 2020

(65) Prior Publication Data
US 2021/0338783 A1  Nov. 4, 2021

Related U.S. Application Data

(60) Provisional application No. 62/742,158, filed on Oct. 5, 2018.

(51) Int. Cl.
*A61K 38/46* (2006.01)
*A61K 38/54* (2006.01)

(52) U.S. Cl.
CPC ............ *A61K 38/465* (2013.01); *A61K 38/54* (2013.01); *C12Y 301/22004* (2013.01); *C12Y 306/04012* (2013.01)

(58) Field of Classification Search
CPC .................. A61K 38/465; A61K 38/54; C12Y 301/22004; C12Y 306/04012
See application file for complete search history.

(56) References Cited

U.S. PATENT DOCUMENTS

| | | | |
|---|---|---|---|
| 8,999,291 B2 * | 4/2015 | Goodman | ........... C07K 16/1275 |
| 2014/0356389 A1 | 12/2014 | Masignani et al. | |
| 2016/0194384 A1 | 7/2016 | Goodman et al. | |
| 2017/0182205 A1 | 6/2017 | Zupancic et al. | |

FOREIGN PATENT DOCUMENTS

| | | |
|---|---|---|
| CN | 103097399 A | 5/2013 |
| WO | WO-2011/123396 A1 | 10/2011 |
| WO | WO-2018/129092 A1 | 7/2018 |

OTHER PUBLICATIONS

Rafferty JB, Bolt EL, Muranova TA, Sedelnikova SE, Leonard P, Pasquo A, Baker PJ, Rice DW, Sharples GJ, Lloyd RG. The structure of *Escherichia coli* RusA endonuclease reveals a new Holliday junction DNA binding fold. Structure. Dec. 2003; 11(12): 1557-67. doi: 10.1016/j.str.2003.11.004. PMID: 14656440. (Year: 2003).*
Garcia et al., Molecular Microbiology, 2013, vol. 89, p. 1213-1225. (Year: 2013).*
Chan et al., Nucleic Acids Research, 1998, vol. 26, No. 7, p. 1560-1566. (Year: 1998).*
BLAST search result for SEQ ID No. 1 and NCBI related reference, run on Nov. 1, 2023, 2 pages of PDF. (Year: 2023).*
Ayora et al., "Bacillus subtilis RecU protein cleaves Holliday Junctions and anneals single-stranded DNA", PNAS, vol. 101, No. 2, Jan. 13, 2004, pp. 452-457.
Baslé, et al., "Crystal structure of NucB, a biofilm-degrading endonuclease", Nucleic Acids Research, 2018, vol. 46, No. 1, pp. 473-484.
Extended European Search Report dated May 23, 2022, from application No. 19869388.9.
International Search Report and Written Opinion dated Feb. 19, 2020, from application No. PCT/US2019/054868, 11 pages.
Mahdi et al., "Holliday Junction Resolvases Encoded by Homologous rusA Genes in *Escherichia coli* K-12 and Phage 82", J. Mol. Biol., vol. 257, Jan. 19, 1996, pp. 561-573.
Sharples, et al., "Holliday Junction Processing in Bacteria: Insights from the Evolutionary Conservation of RuvABC, RecG, and RusA", Journal of Bacteriology, Sep. 1999, vol. 181, No. 18., pp. 5543-5550.
Bolt et al., "Substrate Specificity of RusA Resolvase Reveals the DNA Structures Targeted by RuvAB and RecG In Vivo", Molecular Cell, Jul. 2002, vol. 10, pp. 187-198.
Devaraj et al., "The DNABII family of proteins is comprised of the only nucleoid associated proteins required for nontypeable Haemophilus influenzae biofilm structure", MicrobiologyOpen, 2018, 13 pages.
Macmaster et al., "RusA Holliday junction resolvase: DNA complex structure-insights into selectivity and specificity", Nucleic Acids Research, 2006, vol. 34, No. 19, 8 pages.
Whitby et al., "Interactions Between RuvA and RuvC at Holliday Junctions: Inhibition of Junction Cleavage and Formation of a RuvA-RuvC-DNA Complex", J. Mol. Biol., 1996, vol. 264, pp. 878-890.

\* cited by examiner

*Primary Examiner* — Kade Ariani
(74) *Attorney, Agent, or Firm* — Foley & Lardner LLP

(57) ABSTRACT

Provided herein are methods to inhibit or disrupt a bio film comprising contacting the bio film with an agent that cleaves the Holliday junction (HJ) structure in the bio film.

17 Claims, 5 Drawing Sheets

Specification includes a Sequence Listing.

COMPOSITIONS AND METHODS FOR ENZYMATIC DISRUPTION OF BACTERIAL BIOFILMS

CROSS-REFERENCE TO RELATED APPLICATION

This application is a national stage entry under U.S.C. § 371 of International Application No. PCT/US2019/054868, filed Oct. 4, 2019, which in turn claims priority under 35 U.S.C. § 119(e) to U.S. Provisional Application Ser. No. 62/742,158, filed Oct. 5, 2018, the contents of each of which are hereby incorporated by reference in its entirety into the present disclosure.

STATEMENT OF GOVERNMENT SUPPORT

This invention was made with government support under Grant No. R01DC011818 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Apr. 1, 2021, is named 106887-7861_SL.txt and is 19,024 bytes in size.

BACKGROUND

Bacteria adopt a biofilm state that represents multicellular microbial communities adherent to each other as well as to an abiotic or biotic surface. Bacteria in a biofilm are surrounded by extracellular polymeric substances, primarily comprised of exopolysaccharides, extracellular DNA (eDNA) and proteins. eDNA is ubiquitous and a pivotal component to maintain the structural integrity of bacterial biofilms.

Bacteria persisting in a biofilm in the human body cause about two-thirds of all chronic/recurrent diseases. These biofilms are comprised of bacteria protected by an outer "slime" that is often comprised primarily of DNA that prevents the innate and adaptive immune systems, antibiotics and other antibacterial agents from gaining access to the bacteria inside the biofilm, making it extremely difficult to clear the infection from the body. Furthermore, the biofilm can act as a reservoir for future acute infections often with lethal consequences. Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets, and in swimming pools and spas.

Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water.

SUMMARY

Bacteria adopt a biofilm state that represents multicellular microbial communities adherent to each other as well as to an abiotic or biotic surface. Bacteria in a biofilm are surrounded by extracellular polymeric substances, primarily comprised of exopolysaccharides, extracellular DNA (eDNA) and proteins. eDNA is ubiquitous and a pivotal component to maintain the structural integrity of bacterial biofilms. Applicant have shown previously that eDNA in biofilms formed by multiple bacterial species is organized into a lattice-like structure that is stabilized by DNABII proteins. DNABII proteins are a family of DNA binding proteins that exhibit high affinity to pre-bent DNA.

Thus, in one aspect, provided herein is a method to inhibit or disrupt a biofilm, the method comprising, or alternatively consisting essentially of, or yet further consisting of, contacting the biofilm with an agent that cleaves the Holliday junction (HJ) structure in the biofilm. Non-limiting examples of such agents include RusA polypeptide or a RuvABC peptide complex. In one aspect, the contacting is in vitro in a test tube or ex vivo. In another aspect, the contacting is in vivo, and the contacting is achieved by administering the agent to a subject in need thereof. The biofilm or diseases incident to a biofilm infection that can be treated by these methods can be caused by bacterial infections, e.g., infections by the ESKAPE pathogens, UPEC, NTHI, *S. epidermidis, Streptococcus agalactiae, Neisseria meningitidis,* Treponemes, *denticola, pallidum), Burkholderia cepacia),* or *Burkholderia pseudomallei, Haemophilus influenzae* (nontypeable), *Moraxella catarrhalis, Streptococcus pneumoniae, Streptococcus pyogenes, Pseudomonas aeruginosa, Mycobacterium tuberculosis,*

In one aspect, the agent for use in the method comprises, or consists essentially of, or yet consists of an HJ-specific endonuclease, for example RuvABC or RusA.

Also provided is a method to inhibit or disrupt a biofilm or treat a disease or condition incident to a biofilm infection in a subject in need thereof, the method comprising, or alternatively consisting essentially of, or yet further consisting of, administrating to the subject an effective amount of an agent that cleaves the Holliday junction (HJ) structure in the biofilm. The agent can be administered locally or systemically. In one aspect, the agent for use in the method comprises, or consists essentially of, or yet consists of an HJ-specific endonuclease, for example RuvABC or RusA.

In one aspect, the method is used to treat mammals, human patients, or pediatric mammals or human patients.

The biofilm or diseases incident to a biofilm infection that can be treated by these methods can be caused by bacterial infections, e.g., infections by UPEC, NTHI, *S. epidermidis, Streptococcus agalactiae, Neisseria meningitidis,* Treponemes, *denticola, pallidum), Burkholderia cepacia),* or *Burkholderia pseudomallei, Haemophilus influenzae*

(nontypeable), *Moraxella catarrhalis, Streptococcus pneumoniae, Streptococcus pyogenes, Pseudomonas aeruginosa, Mycobacterium tuberculosis*, upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP).

Also provided herein is a RusA protein sequence that comprises, or consists essentially of, or yet further consists of:

(SEQ ID NO: 1)
MVNTYSITLPWPPSNNRYYRHNRGRTHVSAEGQAYRDNVARIIKNAMLDI

GLAMPVKIRIECHMPDRRRRDLDNLQKAAFDALTKAGFWLDDAQVVDYRV

VKMPVTKGGRLELTITEMGNEA, and equivalents thereof, wherein an equivalent contains the mutated amino acids as shown herein (bolded lettering).

Also provided herein is a RuvB protein sequence that comprises, or consists essentially of, or yet further consists of:

(SEQ ID NO: 2)
MIEADRLISAGTTLPEDVADRAIRPKLLEEYVGQPQVRSQMEIFIKAAKL

RGDALDHLLIFGPPGLGKTTLANIVANEMGVNLRTTSGPVLEKAGDLAAM

LTNLEPHDVLFIDEIHRLSPVVEEVLYPAMEDYQLDIMIGEGPAARSIKI

DLPPFTLIGATTRAGSLTSPLRDRFGIVQRLEFYQVPDLQYIVSRSARFM

GLEMSDDGALEVARRARGTPRIANRLLRRVRDFAEVKHDGTISADIAAQA

LDMLNVDAEGFDYMDRKLLLAVIDKFFGGPVGLDNLAAAIGEERETIEDV

LEPYLIQQGFLQRTPRGRMATTRAWNHFGITPPEMPA, and equivalents thereof, wherein an equivalent contains the mutated amino acids as shown herein (bolded lettering).

Also provided herein is a RuvC protein sequence that comprises, or consists essentially of, or yet further consists of:

(SEQ ID NO: 3)
MASAIILGIDPGSRVTGYGVIRQVGRQLSYLGSGCIRTKVDDLPSRLKLI

YAGVTEIITQFQPDYFAIEQVFMAKNADSALKLGQARGVAIVAAVNQELP

VFEYAARQVKQTVVGIGSAEKSQVQHMVRTLLKLPANPQADAADALAIAI

THCHVSQNAMQMSESRLNLARGRLRA, and equivalents thereof, wherein an equivalent contains the mutated amino acids as shown herein (bolded lettering).

Also provided herein is a RuvA, B and C protein complex that comprises, or consists essentially of, or yet further consists of, the combination of sequences, RuvA:

(SEQ ID NO: 4)
MIGRLRGIIIEKQPPLVLIEVGGVGYEVHMPMTCFYELPEAGQEAIVFTH

FVVREDAQLLYGFNNKQERTLFKELIKTNGVGPKLALAILSGMSAQQFVN

AVEREEVGALVKLPGIGKKTAERLIVEMKDRFKGLHGDLFTPAADLVLTS

PASPATDDAEQEAVAALVALGYKPQEASRMVSKIARPDASSETLIREALR

AAL,
and

RuvB:

(SEQ ID NO: 2)
MIEADRLISAGTTLPEDVADRAIRPKLLEEYVGQPQVRSQMEIFIKAAKL

RGDALDHLLIFGPPGLGKTTLANIVANEMGVNLRTTSGPVLEKAGDLAAM

LTNLEPHDVLFIDEIHRLSPVVEEVLYPAMEDYQLDEVIIGEGPAARSIK

IDLPPFTLIGATTRAGSLTSPLRDRFGIVQRLEFYQVPDLQYIVSRSARF

MGLEMSDDGALEVARRARGTPRIANRLLRRVRDFAEVKHDGTISADIAAQ

ALDMLNVDAEGFDYMDRKLLLAVIDKFFGGPVGLDNLAAAIGEERETIED

VLEPYLIQQGFLQRTPRGRMATTRAWNHFGITPPEMPA,
and

RuvC:

(SEQ ID NO: 3)
MASAIILGIDPGSRVTGYGVIRQVGRQLSYLGSGCIRTKVDDLPSRLKLI

YAGVTEIITQFQPDYFAIEQVFMAKNADSALKLGQARGVAIVAAVNQELP

VFEYAARQVKQTVVGIGSAEKSQVQHMVRTLLKLPANPQADAADALAIAI

THCHVSQNAMQMSESRLNLARGRLRA, and equivalents thereof, wherein an equivalent contains the mutated amino acids as shown herein (bolded lettering).

Also provided herein is a recombinant polypeptide comprising, or alternatively consisting essentially of, or yet consisting of, one or more of the isolated polypeptides as described herein, further comprising at least one additional amino acid located at either or both termini.

This disclosure also provides an antibody that binds to, or was raised against a mutated polypeptide as described herein. The antibodies are useful as diagnostic and prognostic agents. Further provided one or more isolated polypeptides and/or antibodies as described herein and a carrier, such as a pharmaceutically acceptable carrier.

This disclosure also provides polynucleotides encoding the isolated polypeptide or antibody as described herein as well as their complements. In one aspect, the polynucleotides are detectably labeled. The polynucleotides can optionally be operatively linked to a promoter and/or enhancer for expression of the polynucleotide. Further provided is a method of recombinantly producing the polypeptides by expressing the polynucleotides in an appropriate expression system such as a host cell, and then producing and isolating the recombinantly produced polypeptides.

Yet further provided is a vector comprising, or alternatively consisting essentially of, or yet consisting of, a polynucleotide as described herein.

In another aspect, provided herein is an isolated host cell comprising one of more of a polypeptide, a polynucleotide, or a vector as described herein. Compositions comprising a carrier and one or more of a polypeptide, a polynucleotide, or a vector as described herein are further provided. In one aspect, the carrier is a pharmaceutically acceptable carrier.

Further provided is a kit comprising an agent that cleaves the Holliday junction (HJ) structure in the biofilm and instructions for use in the methods described herein.

BRIEF DESCRIPTION OF THE FIGURES

(FIG. 1C) Preformed S. epidermidis biofilm was incubated with the indicated protein and and/or antibody for 16 hours. Biofilms were stained with LIVE/DEAD® stain and visualized via CLSM. Images were analyzed by COMSTAT to calculate average thickness and biomass. Percent change in biomass compared to control is plotted, average thickness (not shown) showed identical trends. Bars represent the standard error of the mean (SEM). Statistical significance compared to control was assessed with unpaired t-tests, *p<0.05, p<0.01, *p>0.001. Note that RuvA prevents α-IHF-mediated collapse of the biofilm structure of UPEC, NTHI and S. epidermidis.

(FIG. 3A) UPEC and (FIG. 3B) NTHI biofilms were preformed for 16 hours and then incubated with the indicated antibody and RuvA for 24 hours (total 40 hours). Biofilms were incubated with RuvB and RuvC in the final 16 hours. (FIG. 3C) S. epidermidis biofilm was preformed for 24 hours and then incubated with the indicated protein and and/or antibody for 16 hours. Biofilms were stained with LIVE/DEAD® stain and visualized via CLSM. Images were analyzed by COMSTAT to calculate biomass. Bars represent the SEM. Statistical significance compared to control was assessed with unpaired t-tests, *p<0.05, p<0.01, **p<0.0001. Note that upon replacement of DNABII proteins with RuvA within the biofilm matrix, biofilms were susceptible to HJ specific endonuclease RuvC that resulted in the collapse of UPEC, NTHI and S. epidermidis biofilm structure.

(FIG. 6D) The relative intensity of cruciform DNA was determined by the ratio of cruciform DNA (light gray) to NTHI (gray). Bars represent the SEM. Note the uniform distribution of HJ DNA within an NTHI biofilm (FIG. 6B) and the loss of cruciform DNA in the presence of RusA (FIG. 6C).

DETAILED DESCRIPTION

Definitions

Figures 1A, 1B, 1C:
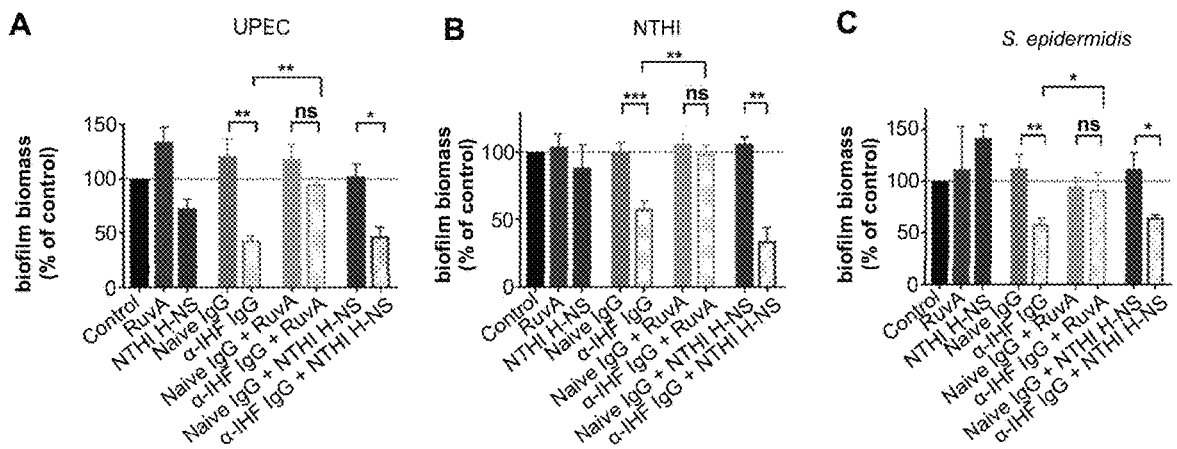
FIGS. 1A-1C: Stabilization of bacterial biofilm structure by Holliday junction (HJ) specific DNA binding protein RuvA. Preformed (FIG. 1A) UPEC and (FIG. 1B) NTHI biofilms were incubated with the indicated protein and/or antibody for 24 hours.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "biofilm" intends a thin layer of microorganisms that adhere to the surface of a structure, that may be organic or inorganic, together with the polymers such as DNA that they secrete. The are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems.

Biofilms also are involved in numerous diseases. For instance, cystic fibrosis patients have *Pseudomonas* infections that often result in antibiotic resistant biofilms.

The term "inhibiting, competing or titrating" intends a reduction in the formation of the DNA/protein matrix.

A "DNA BIT polypeptide or protein" intends a DNA binding protein or polypeptide that is composed of DNA-binding domains and thus have a specific or general affinity for microbial DNA. In one aspect, they bind DNA in the minor grove. A non-limiting example of a DNA BIT protein is an integration host factor (IHF) protein. Other DNA binding proteins that may be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank AccessionNo.: NP_418813).

The DNABII family is a member of a class of proteins referred to as nucleoid associated proteins (NAPs), bacterial proteins that, in part, shape the intracellular bacterial nucleoid (Browning et al. (2010) Curr. Opin. Microbiol. 13:773-780). In addition, this family is ubiquitous, expressed by virtually all eubacteria. All characterized family members to date function as either a homodimer or heterodimer of subunits. The family is divided into two types, HU (histone-like protein) and IHF (integration host factor). The primary distinction between these family members is that HU binds DNA in a sequence independent manner, while IHF binds a consensus sequence (WATCAANNNNTTR (SEQ ID NO: 5) where W is A or T and R is a purine and N is any base conserved across genera (Swinger et al. (2004) Curr. Opin. Struct. Biol. 14:28-35). All DNABII proteins bind to and bend DNA considerably, e.g., *E. coli* IHF can bend DNA into a virtual U-turn (Rice et al. (1996) Cell 87:1295-1306). In addition, all family members have a preference for pre-bent or curved DNA structures, e.g., Holliday junctions, a cruciform-like structure central to DNA recombination. In fact, DNABII proteins function as accessory factors facilitating all intracellular DNA functions, including gene expression, recombination, repair and replication (Swinger et al. (2004) Curr. Opin. Struct. Biol. 14:28-35).

An "integration host factor" of "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms.

"HMGB1 is an high mobility group box (HMGB) 1 protein that is reported to bind to and distort the minor groove of DNA and is an example of an interfering agent. Recombinant or isolated protein and polypeptide is commercially available from Atgenglobal, ProSpecBio, Protein1 and Abnova.

"HU" refers to a class of heterodimeric proteins typically associate with E. coll. HU proteins are known to bind DNA junctions. Related proteins have been isolated from other microorganisms. The complete amino acid sequence of *E. coli* HU was reported by Laine et al. (1980) Eur. J. Biochem. 103(3):447-481. Antibodies to the HU protein are commercially available from Abcam.

As used herein, the ESKAPE pathogens include *Enterococcus faecium, Staphylococcus aureus, Klebsiella pneumoniae, Acinetobacter baumannii, Pseudomonas aeruginosa*, and *Enterobacter* species. These pathogens are the leading cause of nosocomial infections throughout the world.

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA gene or protein. Some non-limiting examples of different strains of *Haemophilus influenzae* include Rd KW20, 86-028NP, R2866, PittGG, PittEE, R2846, and 2019.

RuvABC is a complex of three proteins that mediate branch migration and resolve the Holliday junction created during homologous recombination in bacteria. RuvA and RuvB bind to the four strand DNA structure formed in the Holliday junction intermediate, and migrate the strands through each other, using a putative spooling mechanism. The RuvAB complex can carry out DNA helicase activity, which helps unwind the duplex DNA. The binding of the RuvC protein to the RuvAB complex is thought to cleave the DNA strands, thereby resolving the Holliday junction RuvA is a DNA-binding protein that binds Holliday junctions with high affinity. It is thought that the complex consists of either one or two RuvA tetramers, with charge lined grooves through which the incoming DNA is channeled. The structure also showed the presence of so-called 'acidic pins' in the centre of the tetramer, which serve to separate the DNA duplexes.

RuvB is an ATPase that is only active in the presence of DNA and compared to RuvA, RuvB has a low affinity for DNA. The RuvB proteins are thought to form hexameric rings on the exit points of the newly formed DNA duplexes, and it is proposed that they 'spool' the emerging DNA through the RuvA tetramer.

RuvC is the resolvase, which cleaves the Holliday junction. RuvC proteins have been shown to form dimers in solution and its structure has been solved at 2.5 A. It is thought to bind either on the open, DNA exposed face of a single RuvA tetramer, or to replace one of the two tetramers. Binding is proposed to be mediated by an unstructured loop on RuvC, which becomes structured on binding RuvA. RuvC can be bound to the complex in either orientation, therefore resolving Holliday junctions in either a horizontal or vertical manner.

RusA is endonuclease that resolves Holliday junction intermediates made during homologous genetic recombination and DNA repair. It exhibits sequence and structure-selective cleavage of four-way DNA junctions, where it introduces symmetrical nicks in two strands of the same polarity at the 5' side of CC dinucleotides. It also Corrects the detects in genetic recombination and DNA repair associated with inactivation of ruvAB or ruvC. The sequence and mutation analysis of the protein is disclosed at www.uniprot.org/uniprot/P0AG74, last accessed on Sep. 22, 2019.

"Microbial DNA" intends single or double stranded DNA from a microorganism that produces a biofilm.

"Inhibiting, preventing or breaking down" a biofilm intends the prophylactic or reduction, or therapeutic reduction in the structure of a biofilm. In one aspect, prophylaxis is excluded and only reduction in the structure of a biofilm.

An "interfering agent" intends an agent that any one or more of competes, inhibits, prevents biofilm structure.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

A Holliday junction (HJ) is cross-shaped structure that forms during the process of genetic recombination, when two double-stranded DNA molecules become separated into four strands in order to exchange segments of genetic information. Homologous recombination occurs during meiosis and is characterized by the exchange of genes between a maternal chromatid and a paternal chromatid of a homologous chromosome pair. The two parent DNA molecules, which have long stretches of similar base sequences, are separated into single strands, resulting in base pairing that leads to a four-stranded DNA structure. The Holliday junction travels along the DNA duplex by "unzipping" one strand and reforming the hydrogen bonds on the second strand.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets. In one aspect, the subject is a pediatric or infant subject.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6$^{th}$ ed). Examples of luminescent probes include, but are not limited to, aequorin and luciferases.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

Pharmaceutical compositions suitable for injectable use can include sterile aqueous solutions (where the components are water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer.

A "biologically active agent" or an active agent of this invention intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present invention can be administered for therapy by any suitable route of administration. It will also be appreciated that the preferred route will vary with the condition and age of the recipient, and the disease being treated.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. As used herein, the term "contacting" intends bringing in contact with or to the agent. It will also depend on the nature and sensitivity of the in vitro target and the methods in use. The skilled artisan will be able to determine the effective amount based on these and other considerations. The effective amount may comprise one or more administrations of a composition depending on the embodiment.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacteria produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffiths in in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

As used herein the terms "antibodies" and "immunoglobulin" include antibodies or immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated CDRs or a functional paratope; chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin. a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may comprise conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multi-specific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen of the invention is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

MODES FOR CARRYING OUT THE DISCLOSURE

Compositions

Provided herein are compositions for use in the methods of this disclosure, that is an agent that cleaves the Holliday junction (HJ) structure in a biofilm. In one aspect, the agent is an HJ-specific endonuclease, e.g., RuvABC peptide complex and/or a RusA polypeptide. The amino acid sequences of such include for example the wild-type and mutated as noted below, as well as equivalents thereof, wherein the equivalent maintains the amino acid mutation as described herein. Further provided are the isolated polynucleotides encoding the peptides and polypeptides, vectors and host cells comprising the peptides, polynucleotides, and/or vectors.

In one aspect, provided herein is a RusA protein sequence that comprises, or consists essentially of, or yet further consists of:

```
                                           (SEQ ID NO: 1)
MVNTYSITLPWPPSNNRYYRHNRGRTHVSAEGQAYRDNVARIIKNAMLDI

GLAMPVKIRIECHMPDRRRRDLDNLQKAAFDALTKAGFWLDDAQVVDYRV

VKMPVTKGGRLELTITEMGNEA, and equivalents thereof, wherein an equivalent contains the mutated amino acids as shown herein (bolded lettering).
```

In another aspect, provided herein is a RuvB protein sequence that comprises, or consists essentially of, or yet further consists of:

```
                                           (SEQ ID NO: 2)
MIEADRLISAGTTLPEDVADRAIRPKLLEEYVGQPQVRSQMEIFIKAAKL

RGDALDHLLIFGPPGLGKTTLANIVANEMGVNLRTTSGPVLEKAGDLAAM

LTNLEPHDVLFIDEIHRLSPVVEEVLYPAMEDYQLDIMIGEGPAARSIKI

DLPPFTLIGATTRAGSLTSPLRDRFGIVQRLEFYQVPDLQYIVSRSARFM

GLEMSDDGALEVARRARGTPRIANRLLRRVRDFAEVKHDGTISADIAAQA

LDMLNVDAEGFDYMDRKLLLAVIDKFFGGPVGLDNLAAAIGEERETIEDV

LEPYLIQQGFLQRTPRGRMATTRAWNHFGITPPEMPA, and equivalents thereof, wherein an equivalent contains the mutated amino acids as shown herein (bolded lettering).
```

In a yet further aspect, provided herein is a RuvC protein sequence that comprises, or consists essentially of, or yet further consists of:

```
                                           (SEQ ID NO: 3)
MASAIILGIDPGSRVTGYGVIRQVGRQLSYLGSGCIRTKVDDLPSRLKLI

YAGVTEIITQFQPDYFAIEQVFMAKNADSALKLGQARGVAIVAAVNQELP

VFEYAARQVKQTVVGIGSAEKSQVQHMVRTLLKLPANPQADAADALAIAI

THCHVSQNAMQMSESRLNLARGRLRA, and equivalents thereof, wherein an equivalent contains the mutated amino acids as shown herein (bolded lettering).
```

Also provided herein is a RuvA, B and C protein complex that comprises, or consists essentially of, or yet further consists of, the combination of sequences,

```
RuvA:
                                           (SEQ ID NO: 4)
MIGRLRGIIIEKQPPLVLIEVGGVGYEVHMPMTCFYELPEAGQEAIVFTH

FVVREDAQLLYGFNNKQERTLFKELIKTNGVGPKLALAILSGMSAQQFVN

AVEREEVGALVKLPGIGKKTAERLIVEMKDRFKGLHGDLFTPAADLVLTS

PASPATDDAEQEAVAALVALGYKPQEASRMVSKIARPDASSETLIREALR

AAL,
and

RuvB:
                                           (SEQ ID NO: 2)
MIEADRLISAGTTLPEDVADRAIRPKLLEEYVGQPQVRSQMEIFIKAAKL

RGDALDHLLIFGPPGLGKTTLANIVANEMGVNLRTTSGPVLEKAGDLAAM

LTNLEPHDVLFIDEIHRLSPVVEEVLYPAMEDYQLDEVIIGEGPAARSIK

IDLPPFTLIGATTRAGSLTSPLRDRFGIVQRLEFYQVPDLQYIVSRSARF

MGLEMSDDGALEVARRARGTPRIANRLLRRVRDFAEVKHDGTISADIAAQ

ALDMLNVDAEGFDYMDRKLLLAVIDKFFGGPVGLDNLAAAIGEERETIED

VLEPYLIQQGFLQRTPRGRMATTRAWNHFGITPPEMPA,
and

RuvC:
                                           (SEQ ID NO: 3)
MASAIILGIDPGSRVTGYGVIRQVGRQLSYLGSGCIRTKVDDLPSRLKLI

YAGVTEIITQFQPDYFAIEQVFMAKNADSALKLGQARGVAIVAAVNQELP

VFEYAARQVKQTVVGIGSAEKSQVQHMVRTLLKLPANPQADAADALAIAI

THCHVSQNAMQMSESRLNLARGRLRA, and equivalents thereof, wherein an equivalent contains the mutated amino acids as shown herein (bolded lettering).
```

Also provided herein is a recombinant polypeptide comprising, or alternatively consisting essentially of, or yet consisting of, one or more of the isolated polypeptides as described herein, further comprising at least one additional amino acid located at either or both termini.

It is understood that functional equivalents or variants of the wild type polypeptide or protein also are within the scope of this invention, for example, those having conservative amino acid substitutions of the amino acids, with the equivalent maintains the amino acid mutation as described herein.

In a further aspect, the polypeptides are conjugated or linked to a detectable label. Suitable labels are known in the art and described herein.

In a yet further aspect, the polypeptides with or without a detectable label can be contained or expressed on the surface of a host prokaryotic or eukaryotic host cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this invention also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides of this invention are useful in an in vitro assay system to screen for agents or drugs, which modulate cellular processes.

It is well know to those skilled in the art that modifications can be made to the peptides of the invention to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides of the invention can be modified to include unnatural amino acids. Thus, the peptides may comprise D-amino acids, a combination of and L-amino acids, and various "designer" amino acids (e.g., .beta.-methyl amino acids, C-α.-methyl amino acids, and N-α-methyl amino acids, etc.) to convey special properties to peptides. Additionally, by assigning specific amino acids at specific coupling steps, peptides with α-helices .beta. turns, .beta. sheets, .gamma.-turns, and cyclic peptides can be generated. Generally, it is believed that α-helical secondary structure or random secondary structure is preferred.

The polypeptides of this invention also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides, and adjuvants derived from squalene.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein. In one aspect, the antibodies are selected for the ability to selectively recognize and bind the mutated proteins as described herein.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180, 370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments (VH-CH1-VH-CH1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scFv, and Fv.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

Polynucleotides, Vectors and Host Cells

This disclosure also provides isolated or recombinant polynucleotides encoding one or more of the above-identified polypeptides or antibodies and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides of the disclosure encode polypeptides, proteins, antibodies or fragments thereof having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see Sambrook, et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include prokaryotic and eukaryotic cells, e.g., mammalian cells, animal cells, human cells, simian cells, insect cells, yeast cells, and bacterial cells constructed using known methods. See Sambrook, et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g. a mammalian cell, an animal cell (rat or mouse), a human cell, or a prokaryotic cell such as a bacterial cell, containing a polynucleotide encoding a protein or polypeptide or antibody or fragment thereof.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this disclosure can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides of this disclosure. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide of this disclosure under conditions permitting hybridization (preferably moderately stringent hybridization conditions) of complementary single-stranded polynucleotides, or more preferably, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides of this disclosure can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (1994)) or MacPherson et al. (1991) and (1995), and references cited therein. Alternatively, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide of this disclosure are useful as hybridization probes or as an equivalent of the specific polynucleotides identified herein. Since the full coding sequence of the transcript is known, any portion of this sequence or homologous sequences, can be used in the methods of this disclosure.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region. More preferably, the probe is 85% identical to the corresponding gene sequence after alignment of the homologous region; even more preferably, it exhibits 90% identity.

These probes can be used in radioassays (e.g. Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide of this disclosure. Accordingly, this disclosure also provides a probe comprising or corresponding to a polynucleotide of this disclosure, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally preferred, so as to increase stability and selectivity of the hybrid, and thereby improving the specificity of particular hybrid molecules obtained. More preferably, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

In one aspect, the polypeptides comprising an HMG-box domain include wildtype and recombinantly produced polypeptides and proteins from prokaryotic and eukaryotic host cells.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody and standard techniques such as gel filtration, ion-exchange, reversed-phase and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins of this disclosure by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using the host cell and vector systems described herein.

The polypeptides of this disclosure also can be combined with various solid phase carriers, such as an implant, a stent, a paste, a gel, a dental implant or a medical implant or liquid phase carriers, such as beads, sterile or aqueous solutions, pharmaceutically acceptable carriers, suspensions or emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides and adjuvants derived from squalene.

Compositions

This disclosure also provides a pharmaceutical composition comprising or alternatively consisting essentially of, or yet further consisting of, any of a polypeptide, analog, mutein, or fragment of this disclosure, alone or in combination with each other or other agents, such an antibiotic and an acceptable carrier or solid support. These compositions are useful for various diagnostic and therapeutic methods as described herein.

The agents can be combined with a carrier such as a pharmaceutically acceptable carrier and formulated for local or systemic delivery, e.g., by inhalation or direct injection.

Methods of Use

In one aspect, this disclosure provides method to inhibit or disrupt a biofilm comprising contacting the biofilm with an agent that cleaves the Holliday junction (HJ) structure in the biofilm. The contacting is in vitro or in vivo. In one aspect, the agent is an HJ-specific endonuclease, e.g., RuvABC or RusA. In one aspect, the biofilm is formed by one or more of uropathogenic *Escherichia coli* (UPEC), nontypeable *Haemophilus* influenza (NTHI) or *S. epidermidis*.

Also provided is a method to inhibit or disrupt a biofilm or treat a disease or condition incident to a biofilm infection in a subject in need thereof, comprising administrating to the subject an effective amount of an agent that cleaves the Holliday junction (HJ) structure in the biofilm. In one aspect, the agent is an HJ-specific endonuclease, e.g., Ruv-ABC or RusA.

The subject can be a mammal, such as a human patient or a pediatric human patient. Administration can be local or systemic.

In one aspect, the disease or condition is an infection by UPEC, NTHI or *S. epidermidis, Streptococcus agalactiae, Neisseria meningitidis*, Treponemes, *denticola, pallidum), Burkholderia cepacia*), or *Burkholderia pseudomallei, Haemophilus influenzae* (nontypeable), *Moraxella catarrhalis, Streptococcus pneumoniae, Streptococcus pyogenes, Pseudomonas aeruginosa, Mycobacterium tuberculosis*, upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP).

In one aspect, the disease or condition is cystic fibrosis and the administration is by inhalation therapy or local. In another aspect, the administration or contacting of the agent is performed in the absence of a DNase treatment. In one aspect, the DNAse treatment that is excluded from the therapy comprises an enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In one aspect, the DNase treatment that is excluded from the therapy comprises, or consists essentially of, or yet further consists of, Pulmozyme® (dornase alpha; Genentech, Inc.).

In another aspect, an additional agent, such as an antimicrobial is contacted in vitro or administered to the subject. Administration can be simultaneous or sequential.

Thus, routes of administration applicable to the methods of the disclosure include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods of the disclosure include, but are not limited to, enteral, parenteral or inhalational routes.

Parenteral routes of administration other than inhalation administration include, but are not limited to, topical, transdermal, subcutaneous, intramuscular, intraorbital, intracapsular, intraspinal, intrasternal and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The compounds of the disclosure can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods of the disclosure, the active will be administered orally on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200-about 500 mg and sometimes, depending on the compound, up to as much as about 1 g to about 2.5 g.

Dosing of can be accomplished in accordance with the methods of the disclosure using capsules, tablets, oral suspension, suspension for intra-muscular injection, suspension for intravenous infusion, gel or cream for topical application or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments. In one aspect, the term "treatment" excludes prevention.

The compositions and related methods of the present disclosure may be used in combination with the administration of other therapies, or in the absence of such therapies. These include, but are not limited to, the administration of DNase enzymes, antibiotics, antimicrobials, or other antibodies. In one aspect, the polypeptide is administered with a DNase enzyme to treat a microbial infection and biofilm incident to cystic fibrosis.

In some embodiments, the methods and compositions include a deoxyribonuclease (DNase) enzyme that acts synergistically with a composition of this disclosure, e.g., a DNase. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include minocycline, amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (e.g., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA, anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances, the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formulation or as a separate formulation.

Kits

Kits containing the agents and instructions necessary to perform the in vitro and in vivo methods as described herein also are claimed. Accordingly, the disclosure provides kits for performing these methods which may include a biological agent of this disclosure as well as instructions for carrying out the methods of this disclosure such as collecting tissue and/or performing the screen and/or analyzing the results and/or administration of an effective amount of biological agent as defined herein. These can be used alone or in combination with other suitable antimicrobial agents.

In one embodiment, the present disclosure provides a kit comprising a polypeptide as described herein and instructions for use in breaking down a biofilm or inhibiting, preventing or treating a microbial infection that produces a biofilm. In one embodiment, the kit further comprises one or more of an adjuvant, an antigenic peptide or an antimicrobial. In yet another embodiment, the kit further comprises a carrier selected from the group of a liquid carrier, a pharmaceutically acceptable carrier, a solid phase carrier, a pharmaceutically acceptable carrier, an implant, a stent, a paste, a gel, a dental implant or a medical implant.

Also provided is a kit comprising an agent that cleaves the Holliday junction (HJ) structure in the biofilm and instructions for use in the methods as described herein.

EXPERIMENTAL

Experiment No. 1

To incorporate RuvA, applicant added RuvA (450 nM) to pre-formed biofilms at 16 h and 24 h in the presence of a-DNABII. HJ-specific endonucleases RuvC (100 nM) or RusA (350 nM) were added at 24 h. At 40 h, the biofilms were stained with LIVE/DEAD® or labeled with appropriate antibody for immunofluorescence and analyzed using confocal laser scanning microscopy.

The addition of the prototypic HJ-specific DNA binding protein RuvA, both readily incorporated within the biofilm matrix and prevented a-DNABII-mediated disruption of bacterial biofilms formed by uropathogenic *E. coli*, nontypeable *Haemophilus influenzae* (NTHI), and *Staphylococcus epidermidis*. Next, Applicant assembled the HJ-specific endonuclease complex RuvABC at the RuvA-bound HJ DNA sites, which resulted in collapse of the biofilm structure. Additionally, treatment of bacterial biofilms with another HJ-specific endonuclease RusA, also resulted in total collapse of the biofilm structure of multiple bacterial species. Addition of RusA also prevented the formation of the complex web-like eDNA lattice structure in biofilms formed by NTHI. As a final confirmation for the presence of HJ DNA structure within the biofilm matrix, Applicant labeled bacterial biofilms with a monoclonal antibody directed against cruciform DNA that recognizes HJ DNA and observed uniform distribution of HJ DNA throughout the biofilm matrix. Addition of RusA to biofilms at seeding also dramatically decreased the cruciform DNA within the biofilm matrix.

Collectively, these data indicated that the eDNA lattice of bacterial biofilms are structurally related to HJ recombination intermediates and are critical to the structural integrity of bacterial biofilms.

The Prototypic HJ DNA Binding Protein RuvA Compensates for the Lack of DNABII Proteins in Biofilm Structure Stabilization of UPEC, NTHI and *S. epidermidis*

Figures 2A, 2B, 2C, 2D:
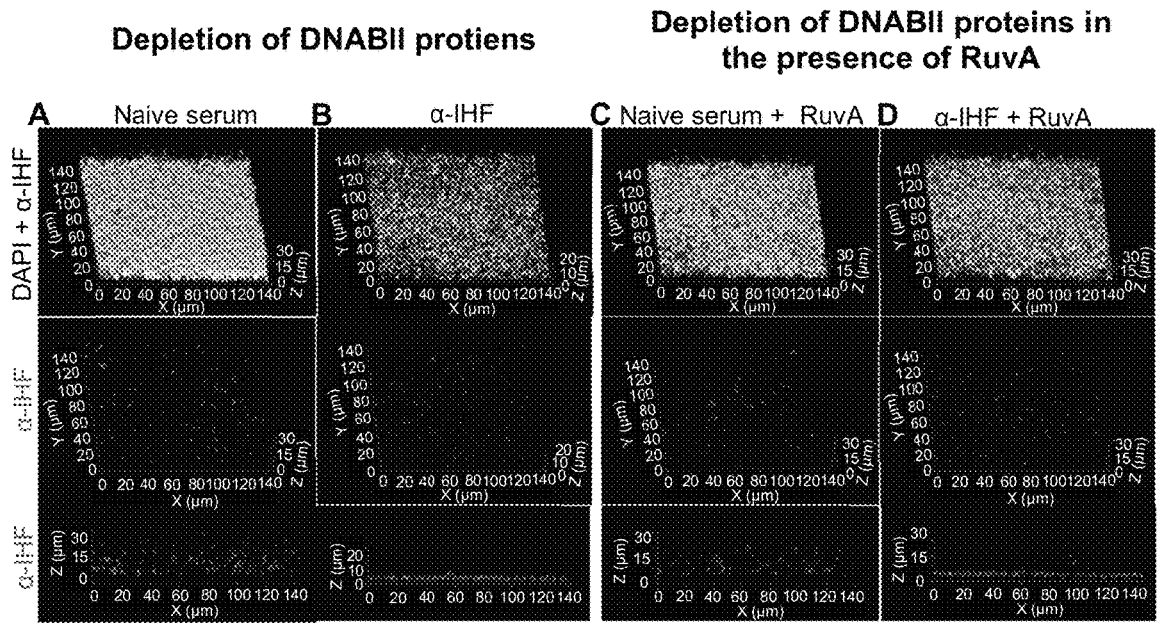
FIGS. 2A-2F: RuvA compensates for the lack of DNABII proteins in biofilm structure stabilization. UPEC biofilms were preformed for 16 hours and then incubated with the indicated protein and/or antibody for 24 hours. Unfixed biofilms were incubated with α-IHF (FIGS. 2A-2D) or α-RuvA (FIG. 2E, FIG. 2F) and then incubated with goat anti-rabbit IgG conjugated to AlexaFluor® 594. UPEC were stained with DAPI (gray). Biofilms were visualized via confocal laser scanning microscope (CLSM). Images represent the top and side view of biofilms. Note that RuvA stabilized biofilm matrix when DNABII proteins were depleted, consistent with HJ-like DNA being the critical structural eDNA element in UPEC.
Figures 2E, 2F:
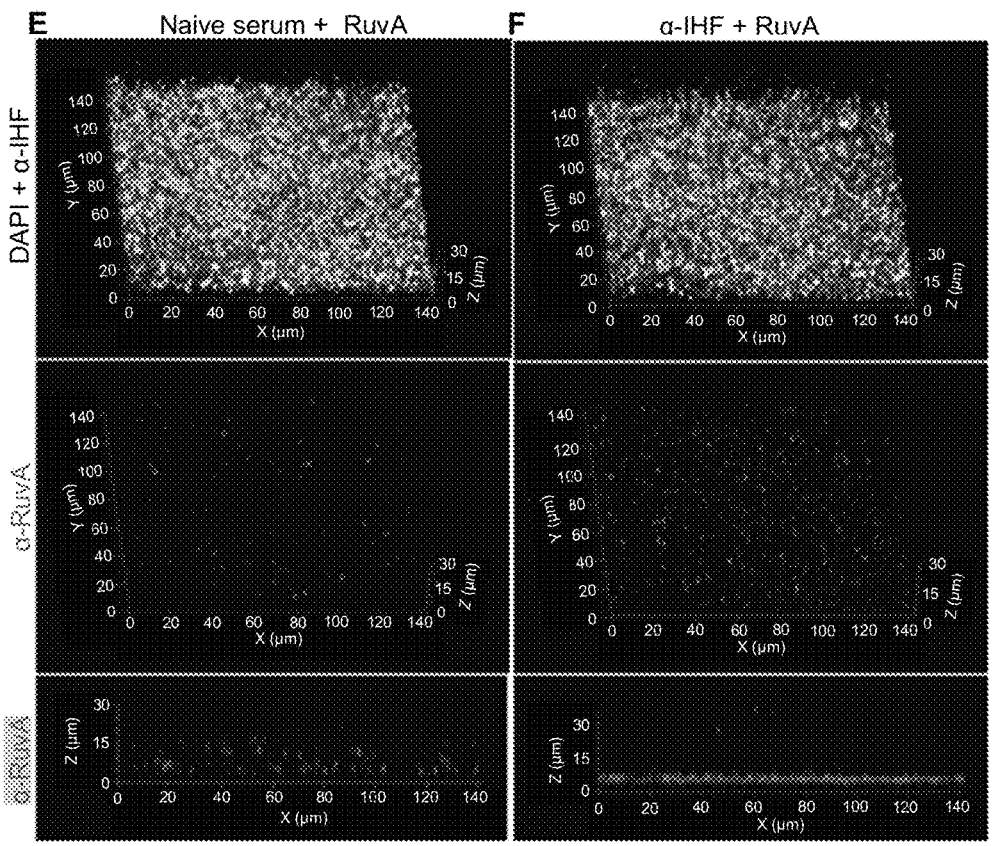
Figures 7A, 7B:
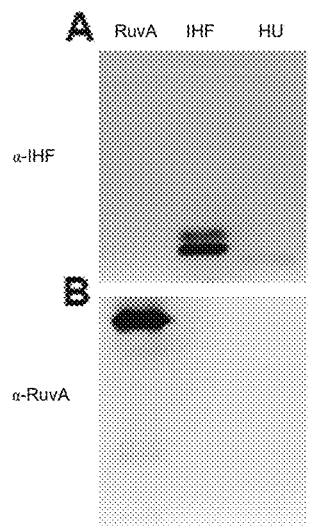
FIGS. 7A-7B: Specificity of α-IHF and α-RuvA antibodies. western blot analysis of DNABII proteins (IHF and HU) and RuvA using the indicated antibody (FIG. 7A) α-IHF (FIG. 7B) α-RuvA. Note that α-IHF and α-RuvA antibodies are specific to their respective target protein.

Applicant have previously demonstrated that eDNA within the biofilm matrix formed by multiple single (Jurcisek et al. (2007), infra.; Goodman, et al. (2011) infra.; and Novotny, et al. (2013), infra.) and mixed bacterial species (Gustave, et al. (2013) infra., Idicula, et al. (2016) et al. infra.) is organized into an interwoven web-like structure that is stabilized by DNABII proteins. Since this organization of eDNA within bacterial biofilms is visually similar to HJ DNA, Applicant tested to confirm that it is structurally related to HJ recombination intermediates. To confirm this, Applicant replaced the DNABII proteins that stabilize the eDNA lattice structure within the extracellular matrix of biofilms formed by UPEC, NTHI and *S. epidermidis* with *E. coli* RuvA, the prototypical HJ binding protein in bacteria. Preformed UPEC, NTHI and *S. epidermidis* biofilms were incubated with a hyperimmune polyclonal antibody directed against *E. coli* IHF (α-IHF) to deplete the DNABII proteins within the extracellular matrix, while RuvA was added in combination with α-IHF such that it can functionally replace DNABII proteins within the biofilm matrix. α-IHF cross-reacts with IHF and HU (FIG. 7), and therefore depletes the DNABII family of proteins that are crucial for the structural stability of the bacterial biofilm matrix. It was evident that α-IHF mediated disruption of biofilms formed by multiple bacteria including UPEC (FIG. 1A), NTHI (FIG. 1B) and *S. epidermidis* (FIG. 1C) could be prevented by the addition of RuvA. Addition of H-NS, a nonspecific DNA binding protein was unable to compensate for the loss of DNABII proteins within the biofilm matrix and thus served as a negative control (FIG. 1). Additionally, Applicant also performed immunofluorescence and confirmed the depletion of DNABII proteins within the extracellular matrix of biofilms formed by UPEC upon treatment with α-IHF (FIGS. 2A, 2B) or upon treatment with α-IHF in the presence of RuvA (FIGS. 2C, 2D), and the concomitant incorporation of RuvA within the biofilm matrix (FIGS. 2E, 2F). The specificities of α-IHF and α-RuvA were determined by western blot analysis and were found to be highly specific for their target protein (FIG. 7). Applicant and others have shown that RuvA exclusively binds HJ DNA with high affinity (Lloyd and Sharples 1993, Rice, Rafferty et al. 1997). Given the high affinity and specificity of RuvA to HJ DNA, this result suggested that RuvA complemented the loss of DNABII proteins and thus stabilized the eDNA structure by selectively binding to HJ DNA that were vacated by DNABII proteins as a result of depletion of DNABII proteins with α-IHF.

Figures 3A, 3B, 3C:
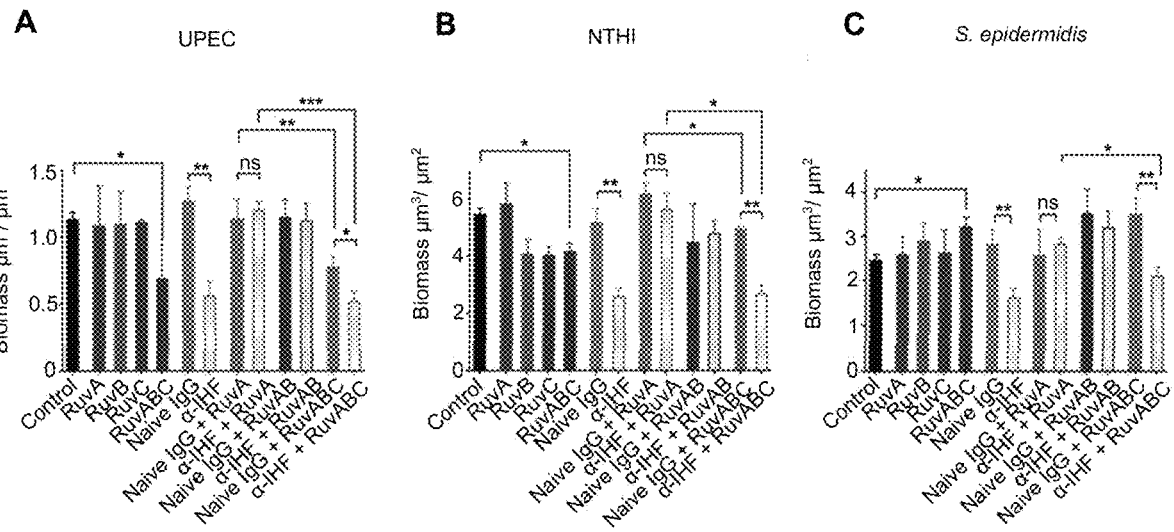
FIGS. 3A-3C: Disruption of bacterial biofilm structure by Holliday junction (HJ) specific endonuclease, RuvC.
Figure 8:
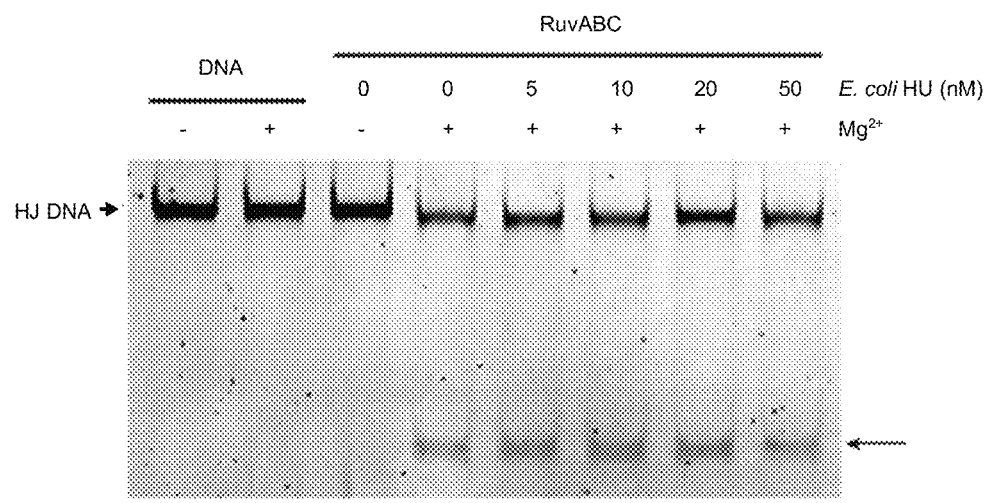
FIG. 8: Cleavage of HJ DNA by RuvABC complex. Free HJ DNA (20 nM) or HJ DNA prebound with the indicated concentration of E. coli HU, was incubated with RuvA (160 nM) and then cleaved with RuvB (240 nM) and RuvC (160 nM) in the presence or absence of $Mg^{2+}$ (10 mM). Location of the cleavage product is indicated with an arrow. Note that RuvABC cleaves free HJ DNA and HJ DNA prebound with E. coli HU in a $Mg^{2+}$ dependent manner.
Figure 9:
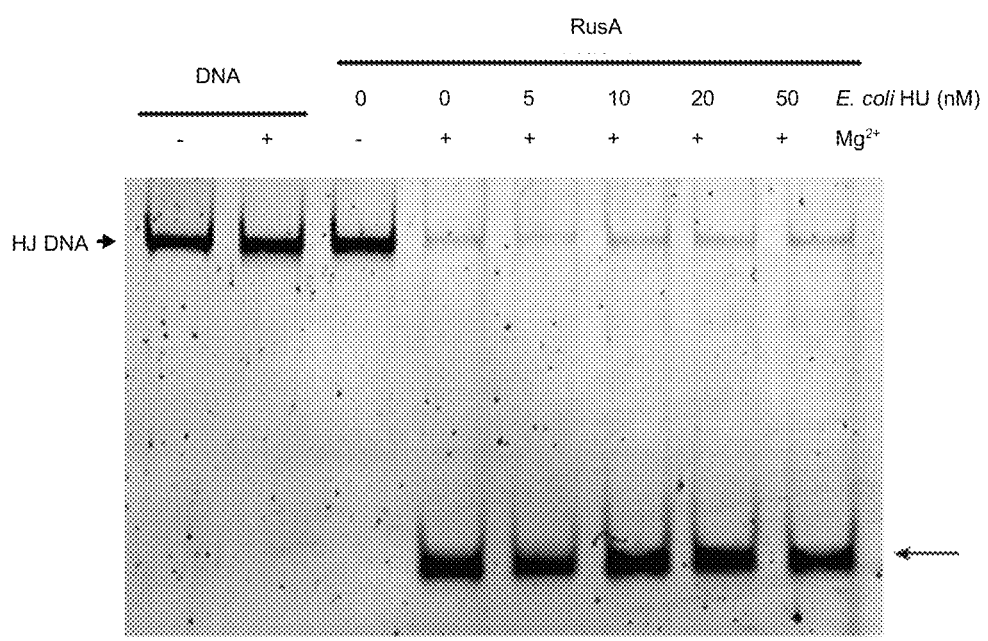
FIG. 9: Cleavage of HJ DNA by RusA. Free HJ DNA (20 nM) or HJ DNA prebound with the indicated concentration of E. coli HU, was incubated with RusA (100 nM) in the presence or absence of $Mg^{2+}$ (10 mM). Location of the cleavage product is indicated with an arrow. Note that RusA cleaves free HJ DNA and HJ DNA prebound with E. coli HU in a $Mg^{2+}$ dependent manner.

Bacterial Biofilm Matrix Stabilized by RuvA is Disrupted Upon Treatment with HJ Specific Endonuclease Complex RuvABC Since RuvA readily and effectively replaced DNABII proteins to maintain the structural stability of biofilms formed by UPEC, NTHI and *S. epidermidis*, Applicant hypothesized that the biofilm matrix stabilized by RuvA is susceptible to disruption by HJ specific endonuclease complex RuvABC. RuvC is the HJ specific endonuclease that resolves HJ DNA into nicked linear duplex DNA. RuvABC complex was shown to cleave a synthetic HJ DNA into duplex DNA (FIG. 8). Next, Applicant preformed UPEC, NTHI and *S. epidermidis* biofilms wherein the DNABII proteins were replaced with RuvA as described above and then incubated the biofilms with RuvABC complex. Strikingly, as evident from FIG. 3, treatment of biofilms in which the matrix was depleted of DNABII proteins and stabilized by RuvA with RuvABC complex (indicated by α-IHF IgG+RuvABC, in FIG. 3) induced a significant reduction in biofilm biomass compared to control biofilms wherein the matrix was stabilized by DNABII proteins (indicated by Naïve IgG+RuvABC, in FIG. 3) in UPEC (FIG. 3A), NTHI (FIG. 3B) and *S. epidermidis* (FIG. 3C). In the absence of the endonuclease RuvC (indicated by, Naïve IgG+RuvAB and α-IHF IgG+RuvAB in FIG. 3), no significant disruption was observed in biofilms formed by UPEC, NTHI and *S. epidermidis*. Collectively, these data suggested that the eDNA lattice structure within biofilms formed by UPEC, NTHI and *S. epidermidis* contain HJ DNA structure that serve a critical structural role in the stability of the bacterial biofilm extracellular matrix.

Figures 4A, 4B, 4C:
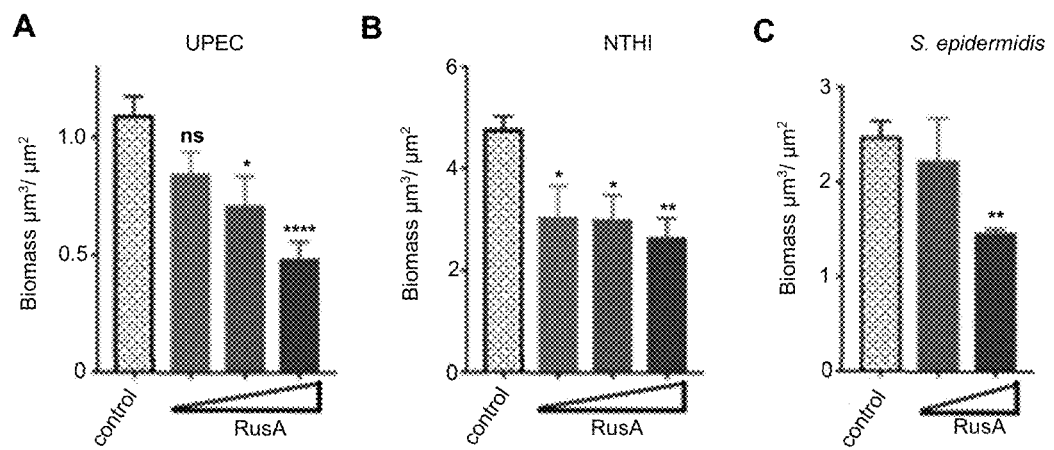
FIGS. 4A-4C: Disruption of bacterial biofilms by Holliday junction specific resolvase, RusA. Preformed (FIG. 4A) UPEC, (FIG. 4B) NTHI and (FIG. 4C) S. epidermidis were incubated with varying concentrations of RusA (1, 5, and 10 µg/ml for UPEC and NTHI; 10 and 20 µg/ml for S. epidermidis) for 16 hours. Biofilms were stained with LIVE/DEAD® stain and visualized via CLSM. Images were analyzed by COMSTAT to calculate biomass and average thickness (not shown). Average thickness showed identical trends. Bars represent the SEM. Statistical significance compared to control was assessed with unpaired t-tests, *p<0.05, p<0.01, *p<0.001. Note that RusA disrupted UPEC, NTHI and S. epidermidis biofilms in a dose-dependent manner.

Bacterial Biofilms are Disrupted Upon Treatment with Another HJ Specific Resolvase. RusA In order to further validate the presence of HJ DNA structure within the bacterial biofilm extracellular matrix, Applicant incubated preformed UPEC, NTHI and *S. epidermidis* biofilms with varying concentrations of RusA, a HJ-specific endonuclease. The activity of RusA was verified by cleavage of a synthetic HJ DNA into duplex DNA as shown in FIG. 4. Treatment with RusA destabilized the biofilm matrix and induced a significant dose-dependent reduction in biofilm biomass compared to control in biofilms formed by UPEC (FIG. 4A), NTHI (FIG. 4B) and *S. epidermidis* (FIG. 4C). RusA binds with very high affinity to HJ and Y-DNA (Chan, Vincent et al. 1998) and only selectively cleaves HJ-DNA. Given the cleavage specificity of RusA, these data suggested that RusA bound to and cleaved HJ DNA within the bacterial biofilm extracellular matrix and therefore disrupted UPEC, NTHI and *S. epidermidis* biofilms.

Figures 5A, 5B, 5C:
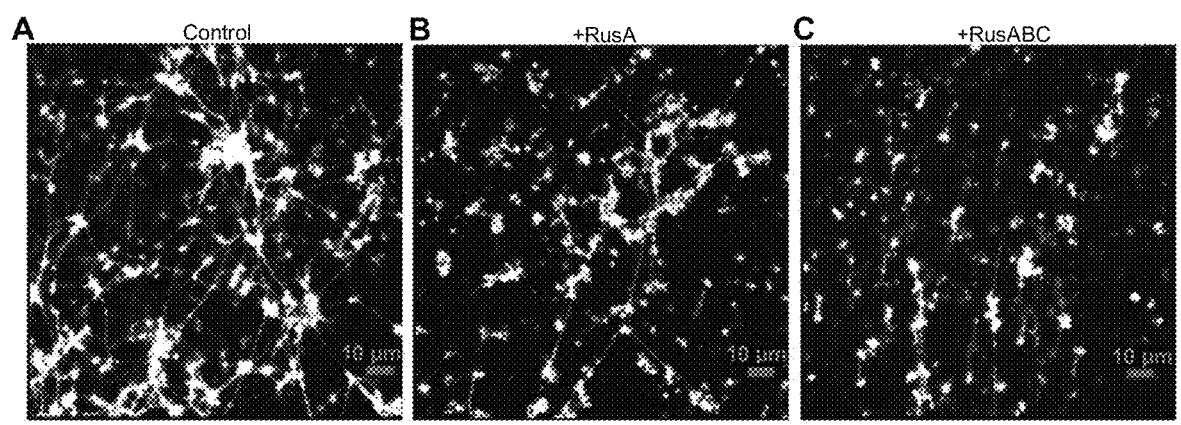
FIGS. 5A-5C: Disruption of lattice-like network of eDNA in an NTHI biofilm by Holliday junction specific endonucleases. NTHI biofilm growth was initiated in the absence (FIG. 5A) or presence (FIG. 5B) of RusA or RuvABC (FIG. 5C) for 16 hours. Unfixed biofilms were incubated with α-DNA monoclonal antibody and then incubated with goat anti-mouse IgG conjugated to AlexaFluor® 488. Biofilms were visualized via CLSM. Note the complex web-like structure of eDNA in the control and the loss of this eDNA structure in the presence of RusA or RuvABC.
Figures 6A, 6B, 6C, 6D:
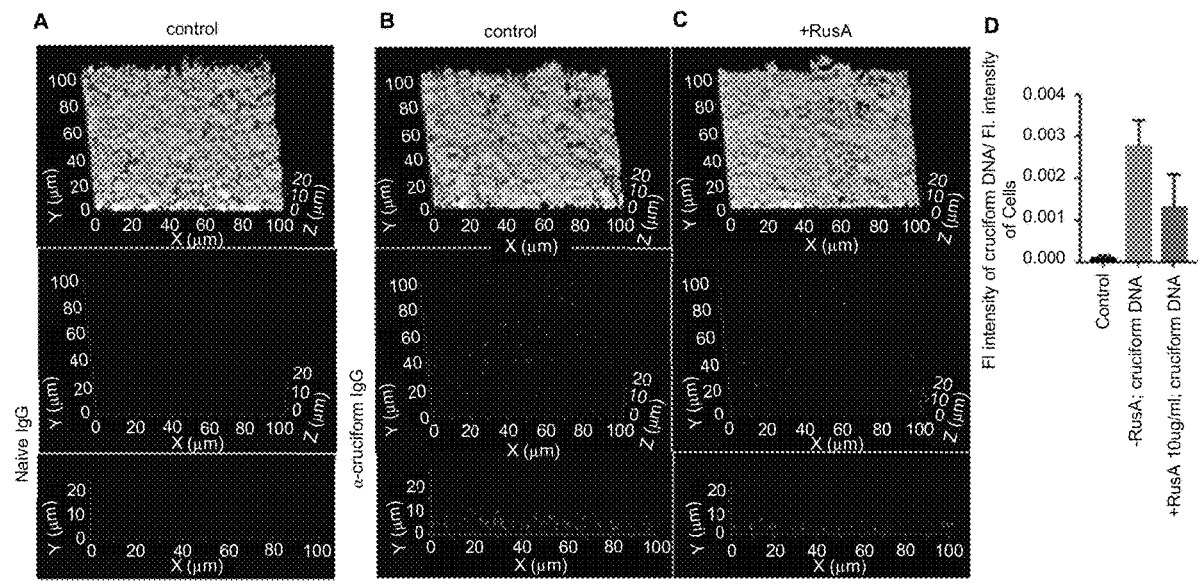
FIGS. 6A-6D: RusA targets HJ-like structures. NTHI biofilm growth was initiated in the absence (FIG. 6A, FIG. 6B) or presence of RusA (10 µg/ml) (FIG. 6C) for 16 hours. Unfixed biofilms were incubated with α-cruciform DNA monoclonal antibody and then incubated with goat anti-mouse IgG conjugated to AlexaFluor® 488 (light gray). NTHI were stained with FilmTracer FM® 4-64 (gray). Biofilms were visualized via CLSM.

RusA and RuvABC Targeted HJ DNA within the Biofilm Extracellular Matrix and Mediated Disruption of the eDNA Lattice-Like Network within an NTHI Biofilm Since treatment of biofilms formed by multiple bacteria with HJ specific endonucleases disrupted biofilms, Applicant reasoned that these endonucleases specifically target HJ DNA structure within the biofilm extracellular matrix to mediate biofilm disruption. In order to visualize the structure of eDNA and evaluate the effect of RusA and RuvABC on the eDNA lattice structure, Applicant formed NTHI biofilms in the absence or presence of RusA or RuvABC for 16 hours at pH 9.0. Applicant then labeled unfixed NTHI biofilms with a monoclonal antibody against double stranded DNA to visualize the eDNA. While the eDNA was organized into a complex web-like structure in the absence of RusA (indicated by control, in FIG. 5), the eDNA lattice structure was completely obliterated in the presence of RusA or RuvABC (FIG. 5). Applicant also labeled these biofilms with a monoclonal antibody against cruciform DNA that specifically binds to the elbow region of a HJ DNA structure (Frappier, Price et al. 1987) to directly visualize Holliday junctions (HJs) within the extracellular matrix of biofilms formed by NTHI. Naïve IgG was used as a negative control (FIG. 6A). In the absence of RusA, HJs were distributed throughout the biofilm matrix as evident from the uniform distribution of the green fluorescence within the biofilm matrix (FIG. 6B). The addition of RusA to biofilms at seeding dramatically decreased the observed green fluorescence (FIG. 6C). Further, in the presence of RusA, the relative abundance of HJ DNA as determined by the ratio of the HJ DNA (α-cruciform labeling) to the bacteria (FilmTracer™) revealed a statistically significant decrease in the amount of HJ DNA within the biofilm matrix compared to the absence of RusA (FIG. 6D). Collectively, these data affirmed the presence and critical significance of HJ DNA for the stability of the bacterial biofilm extracellular matrix.

Methods

Bacteria Strains

NTHI strain 86-028NP isolated from the nasopharynx of a child with chronic otitis media at Nationwide Children's Hospital was used in this study. This strain has been sequenced (Harrison, Dyer et al. 2005) and well characterized (Bakaletz, Tallan et al. 1988, Bakaletz, Leake et al. 1997, Holmes and Bakaletz 1997, Mason, et al. 2003). UPEC strain UTI89 was isolated from a patient with cystitis (Mulvey, Schilling et al. 2001). *S. epidermidis* strain #1618 was isolated from an otitis media patient with serous effusion.

Protein Purification

RuvA gene was cloned in pAM159 and was described in (Sedelnikova, et al. (1997) Acta Crystallogr. D. Biol. Crystallogr. 53(Pt 1): 122-124). Tagless recombinant RuvA was purified on a HiTrap DEAE-Sepharose resin column (GE Healthcare) equilibrated in 40 mM Tris pH 8.5, 2 mM EDTA. The bound protein was eluted with 30 column volumes of a linear gradient of elution buffer containing 40 mM Tris pH 8.5, 2 mM EDTA and 1M NaCl. The fractions containing RuvA were pooled and further purified on a HiTrap Butyl FF resin column (GE Healthcare) equilibrated in 40 mM Tris pH 8.5, 2 mM EDTA, 100 mM NaCl and 1M ammonium sulphate. The bound protein was eluted with elution buffer containing Tris pH 8.5, 2 mM EDTA, 100 mM NaCl and 0 mM-1 M ammonium sulphate using a step gradient. The fractions containing RuvA were pooled and further purified on a HiTrap QFF anion exchange column (GE Healthcare) equilibrated in 40 mM Tris pH 8.5, 2 mM EDTA. The bound protein was eluted with 30 column volumes of a linear gradient of elution buffer containing 40 mM Tris pH 8.5, 2 mM EDTA and 1M NaCl. RuvA was further purified on a HiTrap® Heparin HP column (GE Healthcare) as previously described (Devaraj, Buzzo et al. (2017), infra). Tagless recombinant RuvB, RuvC and RusA were generated using the IMPACT kit (New England Biolabs) as previously described (Novotny et al. (2016), infra.). Each of these genes were PCR amplified from UPEC strain UTI89 genomic DNA using the following oligonucleotides. RuvB: 5'-GCGTGCATATGATTGAAGCAGACCGTCT-GAT—3' (SEQ ID NO: 6) and 5'—GCGTGGCTCTTCCGCACGCCGGCAT-TTCTGGCGGCGTTA—3'(SEQ ID NO: 7). RuvC: 5'—GCGTGCATATGGCTATTATTCTCGGCATTGA—3' (SEQ ID NO: 8) and 5'—GCGTGGCTCTTCCGCACGCACGCAGTCGCCCT-CTCGC—3' (SEQ ID NO: 9). RusA: 5'—GCGTG-CATATGGTGAATACCTACAGCATCACATTACCCTG—3' (SEQ ID NO: 10) and 5'—GCGTGGCTCTTCCGCACGCTTCATTCCCCAT-TTCGGTG—3' (SEQ ID NO: 11). The PCR products were cloned into pTXB1 vector as described in (Novotny, et al. (2016), infra.). The constructs were transformed into the *E. coli* expression strain ER2566 (New England Biolabs) and selected on LB agar containing 100 µg ampicillin/ml. Each of these proteins were overexpressed and purified on a chitin resin column as described (Novotny, et al. (2016) EBioMedicine 10:33-44). RuvB was further purified on a DEAE-Sepharose resin column (GE Healthcare) equilibrated in 40 mM Tris pH 8.5, 2 mM EDTA. The bound protein was eluted with 30 column volumes of a linear gradient of elution buffer containing 40 mM Tris pH 8.5, 2 mM EDTA and 1M NaCl. RuvC and RusA were further purified on a HiTrap® Heparin HP column (GE Healthcare) as previously described (Devaraj, Buzzo et al. (2017) MicrobiologyOpen). The proteins were concentrated in a centrifugal filter (3000 MWCO) and dialyzed in storage buffer (50 mM Tris pH 7.4, 600 mM KCl, 1 mM EDTA, 10% glycerol) for long-term storage at −80° C. All proteins were purified using AKTA pure system (GE Healthcare). Protein concentrations were determined by Pierce BCA protein assay kit (Thermo Fisher Scientific).

Purification of IgG from Serum

Applicant purified IgG from rabbit naïve serum or rabbit polyclonal antiserum directed against *E. coli* IHF (α-IHF) with HiTrap Protein G HP column (GE Healthcare) as described in (Devaraj, Buzzo et al. 2017).

Stabilization of Bacterial Biofilm Structure by RuvA and Disruption by RuvABC Complex NTHI strain 86-028NP was cultured on chocolate agar for 18-20 h at 37° C., in a humidified atmosphere containing 5% $CO_2$, and then suspended in brain heart infusion broth (BHI) supplemented with heme (2 µg/ml) and β-NAD (2 µg/ml) (sBHI) to an OD of 0.65 at 490 nm. Cultures were diluted (1:6) in sBHI broth, and then incubated statically at 37° C., 5% $CO_2$ for 3 hours. The cultures were diluted in sBHI broth to contain $2.5*10^5$ CFU/ml, and 200 µl of this suspension was inoculated into each well of an eight-well chambered cover glass slide (Fisher Scientific). UPEC strain UTI89 was cultured on LB agar for 18-20 h at 37° C., in a humidified atmosphere containing 5% $CO_2$, and then suspended in LB broth to an OD of 0.65 at 490 nm. Cultures were diluted (1:12) in LB broth, and then incubated statically at 37° C., 5% $CO_2$ for 2.5 hours. The cultures were diluted in LB broth to contain $2.5*10^5$ CFU/ml, and 200 µl of this suspension was inoculated into each well of an eight-well chambered cover glass slide. *S. epidermidis* was cultured on chocolate agar for 18-20 h at 37° C., in a humidified atmosphere containing 5% $CO_2$, and then suspended in tryptic soy broth (TSB) to an OD of 0.65 at 490 nm. Cultures were diluted (1:6) in TSB, and then incubated statically at 37° C., 5% $CO_2$ for 3 hours. The cultures were diluted in TSB to contain $2.5*10^5$ CFU/ml, and 200 µl of this suspension was inoculated into each well of an eight-well chambered cover glass slide. After 16 h of incubation of each of the bacterial species at 37° C., 5% $CO_2$, the medium was replaced with fresh medium (control) or fresh medium containing one of the following: naïve IgG (150 µg/ml), α-IHF IgG (150 µg/ml), RuvA (450 nM), H-NS (450 nM), naïve IgG+RuvA, α-IHF+RuvA, naïve IgG+H-NS, or α-IHF+H-NS. In case of *S. epidermidis*, 300 µg/ml of naïve and α-IHF IgG were used. After an additional 8 h incubation period, the medium was replaced again as described above and the chambered cover glass slides were incubated for an additional 16 h. In order to evaluate biofilm disruption by RuvABC complex, at 24 hours biofilms were incubated with RuvB (1130 nM) and RuvC (90 nM) in combination with naïve IgG+RuvA or α-IHF+RuvA for 16 hours. At 40 hours, biofilms were either prepared for immunofluorescence (see below) or washed twice with saline (0.9% NaCl) and stained with LIVE/DEAD® stain (Molecular probes, Eugene, Oreg.) according to the manufacturer's instructions. Biofilms were fixed, imaged and analyzed as described in (Devaraj, Buzzo et al. 2017). All in vitro biofilm assays were repeated a minimum of three times on separate days. Data are presented as mean values±SEM.

Detection of DNABII Proteins and RuvA within Bacterial Biofilms by Immunofluorescence Biofilms formed by NTHI strain 86-028NP, UPEC strain UTI89 and *S. epidermidis* were established on an 8-well chambered cover glass for 24 hours as described above in section 'Stabilization of bacterial biofilm structure'. Immunofluorescence was performed as described in (Devaraj, Buzzo et al. 2017). Briefly, unfixed 40 hour biofilms were incubated with α-IHF (1:200) or antiserum directed against *E. coli* RuvA (α-RuvA; Abcam) (1:200) in phosphate buffered saline (PBS) for 1 hour at room temperature. The biofilms were washed once with PBS and then incubated with goat anti-rabbit IgG conjugated to AlexaFluor® 594 (Molecular Probes) in PBS for 1 hour at room temperature. The biofilms were washed once with PBS and then stained with DAPI (200 µg/ml) in PBS for 10 min. The biofilms were washed once with PBS and then imaged using a ×63 objective on a Zeiss 510 Meta-laser scanning confocal microscope (Zeiss). Three-dimensional images were reconstructed with AxioVision Rel. 4.8 (Zeiss).

Disruption of Bacterial Biofilms by RusA

Biofilms formed by NTHI strain 86-028NP, UPEC strain UTI89 and *S. epidermidis* were established on an 8-well chambered cover glass for 24 hours as described above in section 'Stabilization of bacterial biofilm structure'. Biofilm disruption assay was performed as described in (Devaraj, Buzzo et al. 2017). At 24 hours, biofilms were incubated with varying concentration of RusA (1-20 µg/ml) for an additional 16 hours. Biofilms were stained, fixed, imaged and analyzed as described in (Devaraj, Buzzo et al. 2017). All in vitro biofilm assays were repeated a minimum of three times on separate days. Data are presented as mean values±SEM.

Visualization of eDNA Lattice Structure and Cruciform DNA within Biofilms Formed by NTHI Strain 86-028NP NTHI strain 86-028NP biofilms were formed in the presence or absence of RusA (10 µg/ml) for 16 hours in sBHI adjusted to pH 9.0. At 16 hours, biofilms were washed once with PBS and incubated with 1:200 dilution of mouse α-dsDNA monoclonal antibody (Abcam) to label eDNA or 1:200 dilution of mouse α-cruciform DNA monoclonal antibody (Novus Biologicals) to label cruciform DNA for 1 hour at room temperature. The biofilms were washed once with PBS and then incubated with 1:200 dilution each goat anti-mouse IgG conjugated to AlexaFluor® 488 (Molecular Probes) and FilmTracer FM® 4-64 (Molecular Probes) in PBS at room temperature for 1 hour. The biofilms were washed once with PBS and then imaged using a ×63 objective on a Zeiss 510 Meta-laser scanning confocal microscope (Zeiss). Three-dimensional images were reconstructed with Zen 2012 (Zeiss) to visualize eDNA lattice structure, or AxioVision Rel. 4.8 (Zeiss) to visualize cruciform DNA. The relative abundance of cruciform DNA was quantified as described in (Devaraj, Buzzo et al. 2017).

Electrophoretic Mobility Shift Assay (EMSA)

HJ DNA was generated from the following oligonucleotides:

(SEQ ID NO: 12)
5'-GACGCTGCCGAATTCTGGCTTGCTAGGACATCTTTGCCCACGTTGAC

CC-3', (SEQ ID NO: 13)
5'-6-carboxyfluorescein (FAM)-TGGGTCAACGTGGGCAAAGA

TGTCCTAGCAATGTAATCGTCTATGACGTT-3', (SEQ ID NO: 14)
5'-CAACGTCATAGACGATTACATTGCTAGGACATGCTGTCTAGAGACTA

TCGA-3'
and (SEQ ID NO: 15)
5'-ATCGATAGTCTCTAGACAGCATGTCCTAGCAAGCCAGAATTCGGCAG

CGT-3'.

Y-DNA was generated from the following oligonucleotides:

(SEQ ID NO: 12)
5'-GACGCTGCCGAATTCTGGCTTGCTAGGACATCTTTGCCCACGTTGAC

CC-3', (SEQ ID NO: 13)
5'FAM-TGGGTCAACGTGGGCAAAGATGTCCTAGCAATGTAATCGTCTAT

GACGTT-3'.

Duplex DNA was generated from the following oligonucleotides:

(SEQ ID NO: 13)
5'FAM-TGGGTCAACGTGGGCAAAGATGTCCTAGCAATGTAATCGTCTAT

GACGTT-3'
and (SEQ ID NO: 16)
5'-AACGTCATAGACGATTACATTGCTAGGACATCTTTGCCCACGTTGAC

CCA-3'.

Equimolar concentration of the respective oligonucleotides were mixed and heated to 95° C. for 10 min and then slowly cooled to room temperature to make HJ DNA, Y DNA, and duplex DNA. The HJ, Y, and duplex DNA were resolved using a 6% non-denaturing polyacrylamide gel electrophoresis in 0.5×TBE running buffer at 200 Volts for 2.5 hours and were purified from the gel by crush and soak method (ref). RuvA (concentration) was incubated with 20 nM Holliday junction (HJ) DNA, duplex or Y-DNA in reaction buffer (50 mM Tris pH 7.8, 60 mM KCl, 100 µg/ml BSA, 200 µM EDTA) for 30 minutes at 37° C. The reaction mixtures were then separated using 6% non-denaturing polyacrylamide gel electrophoresis in 0.5×TBE running buffer at 200 Volts for 2.5 hours. The resolved DNA was imaged with a Typhoon FLA 7000 (GE Healthcare).

Cleavage Assay

Cleavage of FAM-labelled HJ DNA by RusA and RuvABC was performed at 37° C. in reaction buffer (please fill in the buffer composition here). DNA products were separated using a 6% non-denaturing polyacrylamide gel electrophoresis in 0.5×TBE running buffer at 200 Volts for 2.5 hours. The resolved DNA was imaged with a Typhoon FLA 7000 (GE Healthcare).

Statistical Evaluation

Statistical significance was assessed by unpaired t-test (GraphPad Prism version 6.0). A p≤0.05 was represented as *, a p≤0.01 was represented by , and a p≤0.001 was represented by *.

Experiment No. 2

A number of oral bacteria (e.g., *Aggregatibacter actinomycetemcomitans*, *Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria will greatly aid in elucidating their pathogenic mechanisms. This example provides a model to test the disclosed polypeptides and compositions and their effechinis in treating oral disease.

The surface of machined titanium dental implants (1.2× 4.5 mm) is modified by grit blasting with A103 (100 μm) and HCl etching (pH 7.8 for 20 min at 80° C.). Machined and nano-textured implants were incubated in TSB medium inoculated with D7S clinical strain of *Aggregatibacter actinomycetemcomitans* (Aa) for 1 to 3 days at 37° C. The bacterial biofilm on the implants are analyzed by SEM, as well as by confocal laser scanning microscopy following staining with LIVE/DEAD® BacLight™. Implants with and without established Aa biofilm are transmucosally placed into the alveolar bone of female rats between premolar and incisor region of the maxillae. To detect the presence of Aa biofilm on the implants placed in vivo, bacterial samples are collected from saliva and the oral surfaces of implants after 2 days. Aa can be detected by culture, as well as by PCR analysis. Micro-CT and histological analysis of peri-implant bone and mucosal tissues can be performed six weeks after implantation. The polypeptides and compositions and attached with the surface as described herein and biofilm and bacterial growth is assayed.

Experiment No. 3

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions of this invention are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Experiment No. 4

This experiment provides a porcine model for pre-clinical testing of the disclosed polypeptides and compositions to treat lung diseases such as COPD and cystic fibrosis. See Stoltz et al. (2010) Science Translational Medicine 2(29): 29ra31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be administered the composition to deliver polypeptides to the lungs of these animals by nebulization to assess the amelioration of the signs of disease and associated pathologies. Alternatively, the polypeptides can be delivered to the lungs of appropriate animal models by nebulization to assess the amelioration of the signs of disease and associated pathologies.

Experiment No. 5

Applicants also provide a pre-clinical model for tuberculosis (TB). See Ordway et al. (2010) Anti. Agents and Chemotherapy 54:1820. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Experiment No. 6

Multiple animal models of catheter/indwelling device biofilm infections are known. See Otto (2009) Nature Reviews Microbiology, 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with E. *Faecalis*, *S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

```
Sequence Listing
Polynucleotide Sequences
RusA (SEQ ID NO: 17):
ATGGTGAATACCTACAGCATCACATTACCCTGGCCTCCGAGCAATAATCG

CTATTACCGCCATAATCGCGGGCGCACGCACGTCAGCGCAGAGGGGCAGG

CATACCGCGATAACGTCGCCCGAATCATTAAAAACGCAATGCTGGATATC

GGCCTGGCTATGCCTGTGAAAATCCGCATTGAGTGCCACATGCCGGATCG

CCGTCGCCGTGACCTGGATAATCTGCAAAAAGCCGCTTTTGACGCACTCA

CTAAAGCAGGTTTCTGGCTGGATGATGCTCAGGTCGTTGATTACCGCGTT

GTGAAGATGCCTGTTACCAAAGGTGGGAGGCTGGAACTGACCATCACCGA

AATGGGGAATGAAGCGTGCATCACGGGAGATGCACTAGTTGCCCTACCCG

AGGGCGAGTCGGTACGCATCGCCGACATCGTGCCGGGTGCGCGGCCCAAC

AGTGACAACGCCATCGACCTGAAAGTCCTTGACCGGCATGGCAATCCCGT

GCTCGCCGACCGGCTGTTCCACTCCGGCGAGCATCCGGTGTACACGGTGC

GTACGGTCGAAGGTCTGCGTGTGACGGGCACCGCGAACCACCCGTTGTTG

TGTTTGGTCGACGTCGCCGGGGTGCCGACCCTGCTGTGGAAGCTGATCGA

CGAAATCAAGCCGGGCGATTACGCGGTGATTCAACGCAGCGCATTCAGCG

TCGACTGTGCAGGTTTTGCCCGCGGGAAACCCGAATTTGCGCCCACAACC

TACACAGTCGGCGTCCCTGGACTGGTGCGTTTCTTGGAAGCACACCACCG

AGACCCGGACGCCCAAGCTATCGCCGACGAGCTGACCGACGGGCGGTTCT

ACTACGCGAAAGTCGCCAGTGTCACCGACGCCGGCGTGCAGCCGGTGTAT

AGCCTTCGTGTCGACACGGCAGACCACGCGTTTATCACGAACGGGTTCGT

CAGCCACGCTACTGGCCTCACCGGTCTGAACTCAGGCCTCACGACAAATC

CTGGTGTATCCGCTTGGCAGGTCAACACAGCTTATACTGCGGGACAATTG

GTCACATATAACGGCAAGACGTATAAATGTTTGCAGCCCCACACCTCCTT

GGCAGGATGGGAACCATCCAACGTTCCTGCCTTGTGGCAGCTTCAATGA

RuvA (SEQ ID NO: 18):
GTGATAGGCAGACTCAGAGGCATCATCATTGAAAAACAACCCCCGCTGGT

GTTAATTGAAGTGGGCGGCGTAGGCTATGAAGTGCATATGCCGATGACCT

GTTTTTATGAACTCCCTGAAGCGGGTCAGGAAGCGATCGTTTTCACCCAC

TTTGTGGTGCGTGAAGACGCGCAACTGCTGTACGGTTTTAACAATAAACA

AGAGCGCACATTGTTCAAAGAGTTGATCAAAACCAACGGCGTCGGCCCGA

AGTTGGCGCTGCGATCCTCTCCGGAATGTCAGCGCAGCAGTTCGTTAAT

GCCGTTGAGCGTGAAGAAGTGGGGGCACTGGTGAAACTGCCGGGTATTGG

CAAAAAACCGCCGAACGCTTGATTGTTGAAATGAAAGACCGATTTAAAG

GTTTGCATGGCGATCTCTTTACGCCAGCCGCCGACCTGGTACTCACGTCT

CCTGCCAGCCCGGCGACCGACGATGCTGAACAAGAAGCGGTTGCCGCGCT

GGTGGCGCTGGGCTATAAACCACAAGAAGCAAGCCGCATGGTGAGCAAAA

TCGCTCGCCCTGACGCCAGCAGTGAAACTTTAATTCGCGAAGCCCTACGC

GCCGCGTTATGA
```

RuvB (SEQ ID NO: 19):
ATGATTGAAGCAGACCGTCTGATTTCTGCCGGTACCACTTTGCCGGAAGA
TGTAGCAGATCGCGCCATTCGCCCCAAATTACTGGAAGAGTATGTTGGTC
AGCCGCAGGTTCGTTCACAGATGGAGATTTTCATCAAAGCAGCGAAACTG
CGCGGCGATGCCCTCGATCATTTGTTGATTTTTGGTCCTCCGGGGTTGGG
TAAAACTACGCTTGCCAACATTGTCGCCAATGAAATGGGCGTTAATTTAC
GCACGACTTCTGGTCCGGTGCTGGAAAAGGCGGGCGATTTGGCTGCGATG
CTCACTAACCTTGAACCGCATGACGTGCTGTTTATTGATGAGATCCACCG
TCTATCGCCAGTTGTTGAAGAAGTGCTGTACCCGGCAATGGAAGACTACC
AACTGGATATCATGATTGGTGAAGGTCCGGCGGCACGCTCCATTAAAATT
GATTTGCCGCCGTTTACCCTGATTGGTGCAACCACGCGCGCAGGTTCGCT
GACATCACCGTTGCGCGACCGTTTTGGTATTGTGCAACGTCTGGAGTTTT
ATCAGGTGCCGGATCTGCAATATATCGTCAGTCGCAGCGCACGCTTTATG
GGGCTTGAGATGAGTGATGACGGCGCGCTGGAAGTTGCTCGTCGCGCTCG
CGGTACGCCGCGCATTGCCAACCGTCTGCTGCGTCGAGTGCGTGATTTCG
CCGAAGTGAAGCACGATGGCACCATCTCGGCAGATATCGCTGCTCAGGCG
CTGGATATGTTGAATGTCGATGCTGAAGGTTTCGATTATATGGACCGCAA
ATTGTTGCTGGCGGTAATCGATAAGTTCTTTGGTGGACCTGTAGGTCTGG
ATAACCTGGCGGCAGCCATTGGCGAAGAACGTGAAACCATTGAGGATGTG
CTGGAACCTTATTTGATTCAGCAAGGCTTTTTGCAGCGTACACCGCGTGG
GCGTATGGCGACGACGCGGGCGTGAATCACTTTGGCATAACGCCGCCAG
AAATGCCGGCGTGCATCACGGGAGATGCACTAGTTGCCCTACCCGAGGGC
GAGTCGGTACGCATCGCCGACATCGTGCCGGGTGCGCGGCCCAACAGTGA
CAACGCCATCGACCTGAAAGTCCTTGACCGGCATGGCAATCCCGTGCTCG
CCGACCGGCTGTTCCACTCCGGCGAGCATCCGGTGTACACGGTGCGTACG
GTCGAAGGTCTGCGTGTGACGGGCACCGCGAACCACCGTTGTTGTGTTT
GGTCGACGTCGCCGGGGTGCCGACCCTGCTGTGGAAGCTGATCGACGAAA
TCAAGCCGGGCGATTACGCGGTGATTAACGCAGCGCATTCAGCGTCGAC
TGTGCAGGTTTTGCCCGCGGGAAACCCGAATTTGCGCCCACAACCTACAC
AGTCGGCGTCCCTGGACTGGTGCGTTTCTTGGAAGCACACCACCGAGACC
CGGACGCCCAAGCTATCGCCGACGAGCTGACCGACGGGCGGTTCTACTAC
GCGAAAGTCGCCAGTGTCACCGACGCCGGCGTGCAGCCGGTGTATAGCCT
TCGTGTCGACACGGCAGACCACGCGTTTATCACGAACGGGTTCGTCAGCC
ACGCTACTGGCCTCACCGGTCTGAACTCAGGCCTCACGACAAATCCTGGT
GTATCCGCTTGGCAGGTCAACACAGCTTATACTGCGGACAATTGGTCAC
ATATAACGGCAAGACGTATAAATGTTTGCAGCCCCACACCTCCTTGGCAG
GATGGGAACCATCCAACGTTCCTGCCTTGTGGCAGCTTCAATGA

RuvC (SEQ ID NO: 20):
ATGGCTAGCGCTATTATTCTCGGCATTGATCCGGGTTCGCGCGTGACCGG
CTACGGCGTCATCCGCCAGGTAGGTAGGCAACTGTCCTACCTGGGTAGCG
GATGCATCCGCACCAAAGTGGATGATTTACCGTCTCGTCTGAAACTCATC
TATGCGGGCGTGACGGAAATCATCACCCAGTTCCAGCCTGATTATTTCGC

CATTGAACAAGTCTTTATGGCAAAGAACGCTGACTCAGCCCTGAAACTGG
GCCAGGCGCGCGGCGTGGCGATTGTGGCGGCGGTGAATCAGGAGTTGCCA
GTATTTGAATACGCGGCACGTCAGGTAAAGCAAACGGTGGTAGGTATTGG
CAGTGCCGAAAAAGCCAGGTGCAGCATATGGTCCGCACCTTGCTGAAAC
TGCCCGCTAATCCACAGGCGGATGCCGCCGATGCGCTGGCGATTGCTATC
ACCCACTGCCACGTTAGTCAGAATGCGATGCAGATGAGCGAATCGCGGCT
GAACCTGGCGAGAGGGCGACTGCGTGCATCACGGGAGATGCACTAGTTGC
CCTACCCGAGGGCGAGTCGGTACGCATCGCCGACATCGTGCCGGGTGCGC
GGCCCAACAGTGACAACGCCATCGACCTGAAAGTCCTTGACCGGCATGGC
AATCCCGTGCTCGCCGACCGGCTGTTCCACTCCGGCGAGCATCCGGTGTA
CACGGTGCGTACGGTCGAAGGTCTGCGTGTGACGGGCACCGCGAACCACC
GTTGTTGTGTTTGGTCGACGTCGCCGGGGTGCCGACCCTGCTGTGGAAG
CTGATCGACGAAATCAAGCCGGGCGATTACGCGGTGATTAACGCAGCGC
ATTCAGCGTCGACTGTGCAGGTTTTGCCCGCGGGAAACCCGAATTTGCGC
CCACAACCTACACAGTCGGCGTCCCTGGACTGGTGCGTTTCTTGGAAGCA
CACCACCGAGACCCGGACGCCCAAGCTATCGCCGACGAGCTGACCGACGG
GCGGTTCTACTACGCGAAAGTCGCCAGTGTCACCGACGCCGGCGTGCAGC
CGGTGTATAGCCTTCGTGTCGACACGGCAGACCACGCGTTTATCACGAAC
GGGTTCGTCAGCCACGCTACTGGCCTCACCGGTCTGAACTCAGGCCTCAC
GACAAATCCTGGTGTATCCGCTTGGCAGGTCAACACAGCTTATACTGCGG
GACAATTGGTCACATATAACGGCAAGACGTATAAATGTTTGCAGCCCCAC
ACCTCCTTGGCAGGATGGGAACCATCCAACGTTCCTGCCTTGTGGCAGCT
TCAATGA

Protein sequences (Bolded Amino acids are
mutations to the wild-type sequence)
Wild-type RusA protein (SEQ ID NO: 21):
         10         20         30         40
MNPYSITLPW PPSNNRYYRH NRGRTHVSAE GQAYRDNVAR
         50         60         70         80
IIKNAMLDIG LAMPVKIRIE CHMPDRRRPD LDNLQKAAFD
         90        100        110        120
ALTKAGFWLD DAQVVDYRVV KMPVTKGGRL ELTITEMGNE Mutated RusA (SEQ ID NO: 1):
MVNTYSITLPWPPSNNRYYRHNRGRTHVSAEGQAYRDNVARIIKNAMLDI
GLAMPVKIRIECHMPDRRRRDLDNLQKAAFDALTKAGFWLDDAQVVDYRV
VKMPVTKGGRLELTITEMGNEA Wild-type RuvA (SEQ ID NO: 4):
MIGRLRGIIIEKQPPLVLIEVGGVGYEVHMPMTCFYELPEAGQEAWFTHF
VVREDAQLLYGFNNKQERTLFKELIKTNGVGPKLALAILSGMSAQQFVNA
VEREEVGALVKLPGIGKKTAERLIVEMKDRFKGLHGDLFTPAADLVLTSP
ASPATDDAEQEAVAALVALGYKPQEASRMVSKIARPDASSETLIREALRA
AL Mutated RuvB (SEQ ID NO: 2):
MIEADRLISAGTTLPEDVADRAIRPKLLEEYVGQPQVRSQMEIFIKAAKL
RGDALDHLLIFGPPGLGKTTLANIVANEMGVNLRTTSGPVLEKAGDLAAM -continued

LTNLEPHDVLFIDEIHRLSPVVEEVLYPAMEDYQLDEVIIGEGPAARSIK

IDLPPFTLIGATTRAGSLTSPLRDRFGIVQRLEFYQVPDLQYIVSRSARF

MGLEMSDDGALEVARRARGTPRIANRLLRRVRDFAEVKHDGTISADIAAQ

ALDMLNVDAEGFDYMDRKLLLAVIDKFFGGPVGLDNLAAAIGEERETIED

VLEPYLIQQGFLQRTPRGRMATTRAWNHFGITPPEMPA

Mutated RuvC (SEQ ID NO: 3):
MASAIILGIDPGSRVTGYGVIRQVGRQLSYLGSGCIRTKVDDLPSRLKLI

YAGVTEIITQFQPDYFAIEQVFMAKNADSALKLGQARGVAIVAAVNQELP

VFEYAARQVKQTVVGIGSAEKSQVQHMVRTLLKLPANPQADAADALAIAI

THCHVSQNAMQMSESRLNLARGRLRA

REFERENCES

1. Bakaletz, L. O., E. R. Leake, J. M. Billy and P. T. Kaumaya (1997). "Relative immunogenicity and efficacy of two synthetic chimeric peptides of fimbrin as vaccinogens against nasopharyngeal colonization by nontypeable *Haemophilus influenzae* in the chinchilla." *Vaccine* 15(9): 955-961.
2. Bakaletz, L. O., B. M. Tallan, T. Hoepf, T. F. DeMaria, H. G. Birck and D. J. Lim (1988). "Frequency of fimbriation of nontypable *Haemophilus influenzae* and its ability to adhere to chinchilla and human respiratory epithelium." *Infect Immun* 56(2): 331-335.
3. Chan, S. N., S. D. Vincent and R. G. Lloyd (1998). "Recognition and manipulation of branched DNA by the RusA Holliday junction resolvase of *Escherichia coli*." *Nucleic Acids Res* 26(7): 1560-1566.
4. Devaraj, A., J. Buzzo, C. J. Rocco, L. O. Bakaletz and S. D. Goodman (2017). "The DNABII family of proteins is comprised of the only nucleoid associated proteins required for nontypeable *Haemophilus influenzae* biofilm structure." *Microbiologyopen*.
5. Frappier, L., G. B. Price, R. G. Martin and M. Zannis-Hadjopoulos (1987). "Monoclonal antibodies to cruciform DNA structures." *J Mol Biol* 193(4): 751-758.
6. Goodman, S. D., K. P. Obergfell, J. A. Jurcisek, L. A. Novotny, J. S. Downey, E. A. Ayala, N. Tjokro, B. Li, S. S. Justice and L. O. Bakaletz (2011). "Biofilms can be dispersed by focusing the immune system on a common family of bacterial nucleoid-associated proteins." *Mucosal Immunol* 4(6): 625-637.
7. Gustave, J. E., J. A. Jurcisek, K. S. McCoy, S. D. Goodman and L. O. Bakaletz (2013). "Targeting bacterial integration host factor to disrupt biofilms associated with cystic fibrosis." *J Cyst Fibros* 12(4): 384-389.
8. Harrison, A., D. W. Dyer, A. Gillaspy, W. C. Ray, R. Mungur, M. B. Carson, H. Zhong, J. Gipson, M. Gipson, L. S. Johnson, L. Lewis, L. O. Bakaletz and R. S. Munson, Jr. (2005). "Genomic sequence of an otitis media isolate of nontypeable *Haemophilus influenzae*: comparative study with *H. influenzae* serotype d, strain KW20." *J Bacteriol* 187(13): 4627-4636.
9. Holmes, K. A. and L. O. Bakaletz (1997). "Adherence of non-typeable *Haemophilus influenzae* promotes reorganization of the actin cytoskeleton in human or chinchilla epithelial cells in vitro." *Microb Pathog* 23(3): 157-166.
10. Idicula, W. A., J. A. Jursicek, N. D. Cass, S. Ali, S. D. Goodman, C. A. Elmaraghy, K. R. Jatana and L. O. Bakaletz (2016). "Identification of biofilms in post-tympanostomy tube otorrhea." *Laryngoscope In Press*.
11. Jurcisek, J. A. and L. O. Bakaletz (2007). "Biofilms formed by nontypeable *Haemophilus influenzae* in vivo contain both double-stranded DNA and type IV pilin protein." *J Bacteriol* 189(10): 3868-3875.
12. Lloyd, R. G. and G. J. Sharples (1993). "Processing of recombination intermediates by the RecG and RuvAB proteins of *Escherichia coli*." *Nucleic Acids Res* 21(8): 1719-1725.
13. Mason, K. M., R. S. Munson, Jr. and L. O. Bakaletz (2003). "Nontypeable *Haemophilus influenzae* gene expression induced in vivo in a chinchilla model of otitis media." *Infect Immun* 71(6): 3454-3462.
14. Mulvey, M. A., J. D. Schilling and S. J. Hultgren (2001). "Establishment of a persistent *Escherichia coli* reservoir during the acute phase of a bladder infection." *Infect Immun* 69(7): 4572-4579.
15. Novotny, L. A., A. O. Amer, M. E. Brockson, S. D. Goodman and L. O. Bakaletz (2013). "Structural stability of *Burkholderia cenocepacia* biofilms is reliant on eDNA structure and presence of a bacterial nucleic acid binding protein." *PLoS One* 8(6): e67629.
16. Novotny, L. A., J. A. Jurcisek, S. D. Goodman and L. O. Bakaletz (2016). "Monoclonal antibodies against DNA-binding tips of DNABII proteins disrupt biofilms in vitro and induce bacterial clearance in vivo." *EBioMedicine* 10: 33-44.
17. Rice, D. W., J. B. Rafferty, P. J. Artymiuk and R. G. Lloyd (1997). "Insights into the mechanisms of homologous recombination from the structure of RuvA." *Curr Opin Struct Biol* 7(6): 798-803.
18. Sedelnikova, S. E., J. B. Rafferty, D. Hargreaves, A. A. Mandi, R. G. Lloyd and D. W. Rice (1997). "Crystallization of *E. coli* RuvA gives insights into the symmetry of a Holliday junction/protein complex." *Acta Crystallogr D Biol Crystallogr* 53(Pt 1): 122-124.

What is claimed is:

1. A method to inhibit or disrupt a biofilm comprising contacting the biofilm with an agent that cleaves the Holliday junction (HJ) structure in the biofilm, wherein the agent is an HJ-specific endonuclease, thereby inhibiting or disrupting said biofilm.

2. The method of claim 1, wherein the contacting is in vitro or in vivo.

3. The method of claim 1, wherein the HJ-specific endonuclease is a RuvABC polypeptide, a RusA polypeptide, or both.

4. The method of claim 3, wherein the RusA polypeptide comprises the polypeptide MVNTYSITLPWPPSNN-RYYRHNRGRTHVSAEGQAYRDNVARIIKNAML-DIGLAMPVKI RIECHMPDRRRRDLDNLQKAAF-DALTKAGFWLDDAQVVDYRVVKMPVTKGGRLELTI TEMGNEA (SEQ ID NO: 1), or an equivalent thereof.

5. The method of claim 3, wherein the RuvABC polypeptide comprises the polypeptides MIGRLRGIBEKQP-PLVLIEVGGVGYEVHMPMTCFYELPEAGQEAIVFTH-FVVREDAQLL YGFNNKQERTLFKE-LIKTNGVGPKLALAILSGMSAQQFVNAVER-EEVGALVKLPGIGKK TAERLIVEMKDRFKGLH-GDLFTPAADLVLTSPASPATDDAEQEAVAALVAL-GYKPQEAS RMVSKIARPDASSETLIREALRAAL (SEQ ID NO: 4); MIEADRLISAGTTLPEDVADRAIR-PKLLEEYVGQPQVRSQMEIFIKAAKLRGDALDHLLIF GPPGLGKTTLANIVANEMGVNLRTTSGPVLEKAGD-LAAMLTNLEPHDVLFIDEIHRLSP VVEEVLYPAMED-YQLDIMIGEGPAARSIKIDLPPFTLIGATTRAGSLT-SPLRDRFGIVQRL EFYQVPDLQYIVSRSARFMGLEMSDDGAL-EVARRARGTPRIANRLLRRVRDFAEVKHD GTISADI-AAQALDMLNVDAEGFDYMDRKLL-LAVIDKFFGGPVGLDNLAAAIGEERETIE DVLEPYLIQQGFLQRTPRGRMAT-TRAWNHFGITPPEMPA (SEQ ID NO: 2); and MASAIILGIDPGSRVTGYGVIRQVGRQLSYLGSG-CIRTKVDDLPSRLKLIYAGVTEIITQFQ PDYFAIEQVF-MAKNADSALKLGQARGVAIVAAVNQELPVFEYAAR-QVKQTVVGIGSAE KSQVQHMVRTLLKLPANPQADAADALA-IAITHCHVSQNAMQMSESRLNLARGRLRA (SEQ ID NO: 3), or an equivalent of each thereof, wherein an equivalent contains the mutated amino acids as shown in the bold font.

6. The method of claim 1, wherein the biofilm is caused by one or more of uropathogenic *Escherichia coli* (UPEC), nontypeable *Haemophilus influenzae* (NTHI), *S. epidermidis, Streptococcus agalactiae, Neisseria meningitidis, Treponema denticola, Treponema pallidum, Burkholderia cepacia, Burkholderia pseudomallei, Moraxella catarrhalis, Streptococcus pneumoniae, Streptococcus pyogenes, Pseudomonas aeruginosa, Mycobacterium tuberculosis, Enterococcus faecium, Staphylococcus aureus, Klebsiella pneumoniae, Acinetobacter baumannii, Pseudomonas aeruginosa,* or *Enterobacter* species.

7. The method of claim 1, further comprising contacting the biofilm with an antimicrobial agent or a deoxyribonuclease (DNase).

8. A method to inhibit or disrupt a biofilm or treat a disease or condition incident to a biofilm infection in a subject in need thereof, comprising administering to the subject an effective amount of an agent that cleaves the Holliday junction (HJ) structure in the biofilm, wherein the agent is an HJ-specific endonuclease, thereby inhibiting or disrupting said biofilm.

9. The method of claim 8, wherein the administration is local or systemic.

10. The method of claim 8, wherein the HJ-specific endonuclease is a RuvABC polypeptide or a RusA polypeptide or both.

11. The method of claim 10, wherein the RusA polypeptide comprises the polypeptide MVNTYSITLPWPPSNN-RYYRHNRGRTHVSAEGQAYRDNVARIIKNAML-DIGLAMPVKI RIECHMPDRRRRDLDNLQKAAFDALTKAGFWLD-DAQVVDYRVVKMPVTKGGRLELTI TEMGNEA (SEQ ID NO: 1), or an equivalent thereof.

12. The method of claim 10, wherein the RuvABC polypeptide comprises the polypeptides MIGRLRG-IBEKQP-PLVLIEVGGVGYEVHMPMTCFYELPEAGQEAIVFT-HFVVREDAQLL YGFNNKQERTLFKE-LIKTNGVGPKLALAILSGMSAQQFVNAVER-EEVGALVKLPGIGKK TAERLIVEMKDRFKGLHGD-LFTPAADLVLTSPASPATDDAEQEAVAALVAL-GYKPQEAS RMVSKIARPDASSETLIREALRAAL (SEQ ID NO: 4); MIEADRLISAGTTLPEDVADRAIR-PKLLEEYVGQPQVRSQMEIFIKAAKLRGDALDHLLIF GPPGLGKTTLANIVANEMGVNLRTTSGPVLEKAGD-LAAMLTNLEPHDVLFIDEIHRLSP VVEEVLYPAMED-YQLDIMIGEGPAARSIKIDLPPFTLIGATTRAGSLT-SPLRDRFGIVQRL EFYQVPDLQYIVSRSARFMGLEMSDDGAL-EVARRARGTPRIANRLLRRVRDFAEVKHD GTISADI-AAQALDMLNVDAEGFDYMDRKLL-LAVIDKFFGGPVGLDNLAAAIGEERETIE DVLEPYLIQQGFLQRTPRGRMAT-TRAWNHFGITPPEMPA (SEQ ID NO: 2); and MASAIILGIDPGSRVTGYGVIRQVGRQLSYLGSG-CIRTKVDDLPSRLKLIYAGVTEIITQFQ PDYFAIEQVF-MAKNADSALKLGQARGVAIVAAVNQELPVFEYAAR-QVKQTVVGIGSAE KSQVQHMVRTLLKLPANPQADAADALA-IAITHCHVSQNAMQMSESRLNLARGRLRA, (SEQ ID NO: 3) or an equivalent of each thereof, wherein an equivalent contains the mutated amino acids as shown in the bold font.

13. The method of claim 8, further comprising administering an effective amount of an antimicrobial agent to the subject.

14. The method of claim 8, wherein the disease or condition is an infection caused by one or more of *Enterococcus faecium, Staphylococcus aureus, Klebsiella pneumoniae, Acinetobacter baumannii, Pseudomonas aeruginosa, Enterobacter* species, uropathogenic *Escherichia coli* (UPEC), nontypeable *Haemophilus influenzae* (NTHI), *S. epidermidis, Streptococcus agalactiae, Neisseria meningitidis, Treponema denticola, Treponema pallidum, Burkholderia cepacia, Burkholderia pseudomallei, Moraxella catarrhalis, Streptococcus pneumoniae, Streptococcus pyogenes, Pseudomonas aeruginosa,* or *Mycobacterium tuberculosis*; an infection in upper, mid and lower airway, otitis, sinusitis, bronchitis, exacerbations of chronic obstructive pulmonary disease (COPD), chronic cough, complications of or primary cause of cystic fibrosis (CF) or community acquired pneumonia (CAP).

15. The method of claim 8, further comprising contacting the biofilm with an antimicrobial agent or a deoxyribonuclease (DNase).

16. The method of claim 8, wherein the disease is cystic fibrosis and the administration is by inhalation.

17. The method of claim 16, further comprising contacting the biofilm with an antimicrobial agent or DNase.

* * * * *

SEQUENCE LISTING

<160> NUMBER OF SEQ ID NOS: 21

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 1

Met Val Asn Thr Tyr Ser Ile Thr Leu Pro Trp Pro Ser Asn Asn
1               5                   10                  15

Arg Tyr Tyr Arg His Asn Arg Gly Arg Thr His Val Ser Ala Glu Gly
                20                  25                  30

Gln Ala Tyr Arg Asp Asn Val Ala Arg Ile Ile Lys Asn Ala Met Leu
                35                  40                  45

Asp Ile Gly Leu Ala Met Pro Val Lys Ile Arg Ile Glu Cys His Met
        50                  55                  60

Pro Asp Arg Arg Arg Asp Leu Asp Asn Leu Gln Lys Ala Ala Phe
65                  70                  75                  80

Asp Ala Leu Thr Lys Ala Gly Phe Trp Leu Asp Asp Ala Gln Val Val
                85                  90                  95

Asp Tyr Arg Val Val Lys Met Pro Val Thr Lys Gly Gly Arg Leu Glu
                100                 105                 110

Leu Thr Ile Thr Glu Met Gly Asn Glu Ala
        115                 120

<210> SEQ ID NO 2
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ile Glu Ala Asp Arg Leu Ile Ser Ala Gly Thr Thr Leu Pro Glu
1               5                   10                  15

Asp Val Ala Asp Arg Ala Ile Arg Pro Lys Leu Leu Glu Glu Tyr Val
                20                  25                  30

Gly Gln Pro Gln Val Arg Ser Gln Met Glu Ile Phe Ile Lys Ala Ala
                35                  40                  45

Lys Leu Arg Gly Asp Ala Leu Asp His Leu Leu Ile Phe Gly Pro Pro
        50                  55                  60

Gly Leu Gly Lys Thr Thr Leu Ala Asn Ile Val Ala Asn Glu Met Gly
65                  70                  75                  80

Val Asn Leu Arg Thr Thr Ser Gly Pro Val Leu Glu Lys Ala Gly Asp
                85                  90                  95

Leu Ala Ala Met Leu Thr Asn Leu Glu Pro His Asp Val Leu Phe Ile
                100                 105                 110

Asp Glu Ile His Arg Leu Ser Pro Val Val Glu Glu Val Leu Tyr Pro
                115                 120                 125

Ala Met Glu Asp Tyr Gln Leu Asp Ile Met Ile Gly Glu Gly Pro Ala
                130                 135                 140

Ala Arg Ser Ile Lys Ile Asp Leu Pro Pro Phe Thr Leu Ile Gly Ala
145                 150                 155                 160

Thr Thr Arg Ala Gly Ser Leu Thr Ser Pro Leu Arg Asp Arg Phe Gly
                165                 170                 175

Ile Val Gln Arg Leu Glu Phe Tyr Gln Val Pro Asp Leu Gln Tyr Ile
                180                 185                 190

Val Ser Arg Ser Ala Arg Phe Met Gly Leu Glu Met Ser Asp Asp Gly
            195                 200                 205

Ala Leu Glu Val Ala Arg Arg Ala Arg Gly Thr Pro Arg Ile Ala Asn
        210                 215                 220
```

```
Arg Leu Leu Arg Arg Val Arg Asp Phe Ala Glu Val Lys His Asp Gly
225                 230                 235                 240

Thr Ile Ser Ala Asp Ile Ala Ala Gln Ala Leu Asp Met Leu Asn Val
                245                 250                 255

Asp Ala Glu Gly Phe Asp Tyr Met Asp Arg Lys Leu Leu Leu Ala Val
            260                 265                 270

Ile Asp Lys Phe Phe Gly Gly Pro Val Gly Leu Asp Asn Leu Ala Ala
        275                 280                 285

Ala Ile Gly Glu Glu Arg Glu Thr Ile Glu Asp Val Leu Glu Pro Tyr
    290                 295                 300

Leu Ile Gln Gln Gly Phe Leu Gln Arg Thr Pro Arg Gly Arg Met Ala
305                 310                 315                 320

Thr Thr Arg Ala Trp Asn His Phe Gly Ile Thr Pro Pro Glu Met Pro
                325                 330                 335

Ala

<210> SEQ ID NO 3
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Ser Ala Ile Ile Leu Gly Ile Asp Pro Gly Ser Arg Val Thr
1               5                   10                  15

Gly Tyr Gly Val Ile Arg Gln Val Gly Arg Gln Leu Ser Tyr Leu Gly
                20                  25                  30

Ser Gly Cys Ile Arg Thr Lys Val Asp Asp Leu Pro Ser Arg Leu Lys
            35                  40                  45

Leu Ile Tyr Ala Gly Val Thr Glu Ile Ile Thr Gln Phe Gln Pro Asp
    50                  55                  60

Tyr Phe Ala Ile Glu Gln Val Phe Met Ala Lys Asn Ala Asp Ser Ala
65                  70                  75                  80

Leu Lys Leu Gly Gln Ala Arg Gly Val Ala Ile Val Ala Ala Val Asn
                85                  90                  95

Gln Glu Leu Pro Val Phe Glu Tyr Ala Ala Arg Gln Val Lys Gln Thr
            100                 105                 110

Val Val Gly Ile Gly Ser Ala Glu Lys Ser Gln Val Gln His Met Val
        115                 120                 125

Arg Thr Leu Leu Lys Leu Pro Ala Asn Pro Gln Ala Asp Ala Ala Asp
    130                 135                 140

Ala Leu Ala Ile Ala Ile Thr His Cys His Val Ser Gln Asn Ala Met
145                 150                 155                 160

Gln Met Ser Glu Ser Arg Leu Asn Leu Ala Arg Gly Arg Leu Arg Ala
                165                 170                 175

<210> SEQ ID NO 4
<211> LENGTH: 203
<212> TYPE: PRT
<213> ORGANISM: Unknown
<220> FEATURE:
<223> OTHER INFORMATION: Description of Unknown:
      Wild-type RuvA sequence
```

<400> SEQUENCE: 4

Met Ile Gly Arg Leu Arg Gly Ile Ile Ile Glu Lys Gln Pro Pro Leu
1               5                   10                  15

Val Leu Ile Glu Val Gly Gly Val Gly Tyr Glu Val His Met Pro Met
            20                  25                  30

Thr Cys Phe Tyr Glu Leu Pro Glu Ala Gly Gln Glu Ala Ile Val Phe
        35                  40                  45

Thr His Phe Val Val Arg Glu Asp Ala Gln Leu Leu Tyr Gly Phe Asn
    50                  55                  60

Asn Lys Gln Glu Arg Thr Leu Phe Lys Glu Leu Ile Lys Thr Asn Gly
65                  70                  75                  80

Val Gly Pro Lys Leu Ala Leu Ala Ile Leu Ser Gly Met Ser Ala Gln
                85                  90                  95

Gln Phe Val Asn Ala Val Glu Arg Glu Val Gly Ala Leu Val Lys
            100                 105                 110

Leu Pro Gly Ile Gly Lys Lys Thr Ala Glu Arg Leu Ile Val Glu Met
            115                 120                 125

Lys Asp Arg Phe Lys Gly Leu His Gly Asp Leu Phe Thr Pro Ala Ala
130                 135                 140

Asp Leu Val Leu Thr Ser Pro Ala Ser Pro Ala Thr Asp Asp Ala Glu
145                 150                 155                 160

Gln Glu Ala Val Ala Ala Leu Val Ala Leu Gly Tyr Lys Pro Gln Glu
                165                 170                 175

Ala Ser Arg Met Val Ser Lys Ile Ala Arg Pro Asp Ala Ser Ser Glu
            180                 185                 190

Thr Leu Ile Arg Glu Ala Leu Arg Ala Ala Leu
            195                 200

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (7)..(10)
<223> OTHER INFORMATION: a, c, t, g, unknown or other

<400> SEQUENCE: 5
watcaannnn ttr                                                          13

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 6
gcgtgcatat gattgaagca gaccgtctga t                                      31

<210> SEQ ID NO 7
<211> LENGTH: 39
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 7
gcgtggctct tccgcacgcc ggcatttctg gcggcgtta                          39

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgtgcatat ggctattatt ctcggcattg a                                  31

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgtggctct tccgcacgca cgcagtcgcc ctctcgc                            37

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcgtgcatat ggtgaatacc tacagcatca cattaccctg                         40

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgtggctct tccgcacgct tcattcccca tttcggtg                           38

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gacgctgccg aattctggct tgctaggaca tctttgccca cgttgaccc               49

<210> SEQ ID NO 13
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 13
tgggtcaacg tgggcaaaga tgtcctagca atgtaatcgt ctatgacgtt            50

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caacgtcata gacgattaca ttgctaggac atgctgtcta gagactatcg a          51

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atcgatagtc tctagacagc atgtcctagc aagccagaat cggcagcgt             50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aacgtcatag acgattacat tgctaggaca tctttgccca cgttgaccca            50

<210> SEQ ID NO 17
<211> LENGTH: 1149
<212> TYPE: DNA
<213> ORGANISM: Unknown
<220> FEATURE:
<223> OTHER INFORMATION: Description of Unknown:
      RusA sequence

<400> SEQUENCE: 17
atggtgaata cctacagcat cacattaccc tggcctccga gcaataatcg ctattaccgc    60
cataatcgcg ggcgcacgca cgtcagcgca gaggggcagg cataccgcga taacgtcgcc   120
cgaatcatta aaaacgcaat gctggatatc ggcctggcta tgcctgtgaa aatccgcatt   180
gagtgccaca tgccggatcg ccgtcgccgt gacctggata atctgcaaaa agccgctttt   240
gacgcactca ctaaagcagg tttctggctg atgatgctc aggtcgttga ttaccgcgtt    300
gtgaagatgc ctgttaccaa aggtgggagg ctggaactga ccatcaccga atggggaat    360 gaagcgtgca tcacgggaga tgcactagtt gccctacccg agggcgagtc ggtacgcatc   420
gccgacatcg tgccgggtgc gcggcccaac agtgacaacg ccatcgacct gaaagtcctt   480
gaccggcatg gcaatcccgt gctcgccgac cggctgttcc actccggcga gcatccggtg   540
tacacggtgc gtacggtcga aggtctgcgt gtgacgggca ccgcgaacca cccgttgttg   600
tgtttggtcg acgtcgccgg ggtgccgacc ctgctgtgga agctgatcga cgaaatcaag   660

```
ccgggcgatt acgcggtgat tcaacgcagc gcattcagcg tcgactgtgc aggttttgcc    720
cgcgggaaac ccgaatttgc gcccacaacc tacacagtcg gcgtccctgg actggtgcgt    780
ttcttggaag cacaccaccg agacccggac gcccaagcta tcgccgacga gctgaccgac    840
gggcggttct actacgcgaa agtcgccagt gtcaccgacg ccggcgtgca gccggtgtat    900
agccttcgtg tcgacacggc agaccacgcg tttatcacga acgggttcgt cagccacgct    960
actggcctca ccggtctgaa ctcaggcctc acgacaaatc ctggtgtatc cgcttggcag   1020
gtcaacacag cttatactgc gggacaattg gtcacatata acggcaagac gtataaatgt   1080
ttgcagcccc acacctcctt ggcaggatgg gaaccatcca acgttcctgc cttgtggcag   1140
cttcaatga                                                           1149
```

<210> SEQ ID NO 18
<211> LENGTH: 612
<212> TYPE: DNA
<213> ORGANISM: Unknown
<220> FEATURE:
<223> OTHER INFORMATION: Description of Unknown:
    RuvA sequence

<400> SEQUENCE: 18

```
gtgataggca gactcagagg catcatcatt gaaaaacaac ccccgctggt gttaattgaa     60
gtgggcggcg taggctatga agtgcatatg ccgatgacct gttttatga actccctgaa    120 gcgggtcagg aagcgatcgt tttcacccac tttgtggtgc gtgaagacgc gcaactgctg    180
tacggtttta acaataaaca agagcgcaca ttgttcaaag agttgatcaa accaacggc    240 gtcggcccga agttggcgct ggcgatcctc tccggaatgt cagcgcagca gttcgttaat    300
gccgttgagc gtgaagaagt gggggcactg gtgaaactgc cgggtattgg caaaaaaacc    360
gccgaacgct tgattgttga aatgaaagac cgatttaaag gtttgcatgg cgatctcttt    420
acgccagccg ccgacctggt actcacgtct cctgccagcc cggcgaccga cgatgctgaa    480
caagaagcgg ttgccgcgct ggtggcgctg ggctataaac cacaagaagc aagccgcatg    540
gtgagcaaaa tcgctcgccc tgacgccagc agtgaaactt taattcgcga agccctacgc    600
gccgcgttat ga                                                        612
```

<210> SEQ ID NO 19
<211> LENGTH: 1794
<212> TYPE: DNA
<213> ORGANISM: Unknown
<220> FEATURE:
<223> OTHER INFORMATION: Description of Unknown:
    RuvB sequence

<400> SEQUENCE: 19

```
atgattgaag cagaccgtct gatttctgcc ggtaccactt tgccggaaga tgtagcagat     60
cgcgccattc gccccaaatt actggaagag tatgttggtc agccgcaggt tcgttcacag    120
atggagattt tcatcaaagc agcgaaactg cgcggcgatg ccctcgatca tttgttgatt    180
tttggtcctc cggggttggg taaaactacg cttgccaaca ttgtcgccaa tgaaatgggc    240
gttaatttac gcacgacttc tggtccggta ctggaaaagg cgggcgattt ggctgcgatg    300
ctcactaacc ttgaaccgca tgacgtgctg tttattgatg agatccaccg tctatcgcca    360
gttgttgaag aagtgctgta cccggcaatg gaagactacc aactggatat catgattggt    420
gaaggtccgg cggcacgctc cattaaaatt gatttgccgc cgtttaccct gattggtgca    480
accacgcgcg caggttcgct gacatcaccg ttgcgcgacc gttttggtat tgtgcaacgt    540
```

```
ctggagtttt atcaggtgcc ggatctgcaa tatatcgtca gtcgcagcgc acgctttatg    600
gggcttgaga tgagtgatga cggcgcgctg aagttgctc gtcgcgctcg cggtacgccg     660
cgcattgcca accgtctgct gcgtcgagtg cgtgatttcg ccgaagtgaa gcacgatggc    720
accatctcgg cagatatcgc tgctcaggcg ctggatatgt tgaatgtcga tgctgaaggt    780
ttcgattata tggaccgcaa attgttgctg gcggtaatcg ataagttctt tggtggacct    840
gtaggtctgg ataacctggc ggcagccatt ggcgaagaac gtgaaaccat tgaggatgtg    900
ctggaacctt atttgattca gcaaggcttt ttgcagcgta caccgcgtgg gcgtatggcg    960
acgacgcggg cgtggaatca ctttggcata acgccgccag aaatgccggc gtgcatcacg    1020
ggagatgcac tagttgccct acccgagggc gagtcggtac gcatcgccga catcgtgccg    1080
ggtgcgcggc ccaacagtga caacgccatc gacctgaaag tccttgaccg gcatggcaat    1140
cccgtgctcg ccgaccggct gttccactcc ggcgagcatc cggtgtacac ggtgcgtacg    1200
gtcgaaggtc tgcgtgtgac gggcaccgcg aaccacccgt tgttgtgttt ggtcgacgtc    1260
gccggggtgc cgaccctgct gtggaagctg atcgacgaaa tcaagccggg cgattacgcg    1320
gtgattcaac gcagcgcatt cagcgtcgac tgtgcaggtt ttgcccgcgg gaaacccgaa    1380
tttgcgccca caacctacac agtcggcgtc cctggactgg tgcgtttctt ggaagcacac    1440
caccgagacc cggacgccca gctatcgcc gacgagctga ccgacgggcg gttctactac     1500
gcgaaagtcg ccagtgtcac cgacgccggc gtgcagccgg tgtatagcct tcgtgtcgac    1560
acggcagacc acgcgtttat cacgaacggg ttcgtcagcc acgctactgg cctcaccggt    1620
ctgaactcag gcctcacgac aaatcctggt gtatccgctt ggcaggtcaa cacagcttat    1680
actgcgggac aattggtcac atataacggc aagacgtata atgtttgca gccccacacc    1740 tccttggcag gatgggaacc atccaacgtt cctgccttgt ggcagcttca atga           1794
```

<210> SEQ ID NO 20
<211> LENGTH: 1307
<212> TYPE: DNA
<213> ORGANISM: Unknown
<220> FEATURE:
<223> OTHER INFORMATION: Description of Unknown:
      RuvC sequence

<400> SEQUENCE: 20

```
atggctagcg ctattattct cggcattgat ccgggttcgc gcgtgaccgg ctacggcgtc      60
atccgccagg taggtaggca actgtcctac ctgggtagcg gatgcatccg caccaaagtg     120
gatgatttac cgtctcgtct gaaactcatc tatgcgggcg tgacggaaat catcacccag     180
ttccagcctg attatttcgc cattgaacaa gtctttatgg caagaaacgc tgactcagcc     240
ctgaaactgg ccaggcgcg cggcgtggcg attgtggcgg cggtgaatca ggagttgcca     300
gtatttgaat acgcggcacg tcaggtaaag caaacggtgg taggtattgg cagtgccgaa     360
aaaagccagg tgcagcatat ggtccgcacc ttgctgaaac tgcccgctaa tccacaggcg     420
gatgccgccg atgcgctggc gattgctatc acccactgcc acgttagtca gaatgcgatg     480
cagatgagcg aatcgcggct gaacctgcg agagggcgac tgcgtgcatc acggagatg       540 cactagttgc cctacccgag ggcgagtcgg tacgcatcgc cgacatcgtg ccgggtgcgc     600
ggcccaacag tgacaacgcc atcgacctga agtccttga ccggcatggc aatcccgtgc      660
tcgccgaccg gctgttccac tccggcgagc atccggtgta cacggtgcgt acggtcgaag    720
gtctgcgtgt gacgggcacc gcgaaccacc cgttgttgtg tttggtcgac gtcgccgggg    780
```

```
tgccgaccct gctgtggaag ctgatcgacg aaatcaagcc gggcgattac gcggtgattc    840
aacgcagcgc attcagcgtc gactgtgcag gttttgcccg cgggaaaccc gaatttgcgc    900
ccacaaccta cacagtcggc gtccctggac tggtgcgttt cttggaagca caccaccgag    960
acccggacgc ccaagctatc gccgacgagc tgaccgacgg gcggttctac tacgcgaaag   1020
tcgccagtgt caccgacgcc ggcgtgcagc cggtgtatag ccttcgtgtc gacacggcag   1080
accacgcgtt tatcacgaac gggttcgtca gccacgctac tggcctcacc ggtctgaact   1140
caggcctcac gacaaatcct ggtgtatccg cttggcaggt caacacagct tatactgcgg   1200
gacaattggt cacatataac ggcaagacgt ataaatgttt gcagccccac acctccttgg   1260
caggatggga accatccaac gttcctgcct tgtggcagct tcaatga                 1307
```

<210> SEQ ID NO 21
<211> LENGTH: 120
<212> TYPE: PRT
<213> ORGANISM: Escherichia coli

<400> SEQUENCE: 21

```
Met Asn Thr Tyr Ser Ile Thr Leu Pro Trp Pro Pro Ser Asn Asn Arg
1               5                   10                  15

Tyr Tyr Arg His Asn Arg Gly Arg Thr His Val Ser Ala Glu Gly Gln
            20                  25                  30

Ala Tyr Arg Asp Asn Val Ala Arg Ile Ile Lys Asn Ala Met Leu Asp
        35                  40                  45

Ile Gly Leu Ala Met Pro Val Lys Ile Arg Ile Glu Cys His Met Pro
    50                  55                  60

Asp Arg Arg Arg Arg Asp Leu Asp Asn Leu Gln Lys Ala Ala Phe Asp
65                  70                  75                  80

Ala Leu Thr Lys Ala Gly Phe Trp Leu Asp Asp Ala Gln Val Val Asp
                85                  90                  95

Tyr Arg Val Val Lys Met Pro Val Thr Lys Gly Gly Arg Leu Glu Leu
                100                 105                 110

Thr Ile Thr Glu Met Gly Asn Glu
            115                 120
```